United States Patent
Cederna et al.

(10) Patent No.: US 9,808,616 B2
(45) Date of Patent: Nov. 7, 2017

(54) REGENERATIVE PERIPHERAL NERVE INTERFACE

(75) Inventors: Paul S. Cederna, Milan, MI (US); Melanie G. Urbanchek, Ann Arbor, MI (US); David C. Martin, Lincoln University, PA (US)

(73) Assignees: THE REGENTS OF THE UNIVERSITY OF MICHIGAN, Ann Arbor, MI (US); UNIVERSITY OF DELAWARE, Newark, DE (US)

( * ) Notice: Subject to any disclaimer, the term of this patent is extended or adjusted under 35 U.S.C. 154(b) by 497 days.

(21) Appl. No.: 13/979,507

(22) PCT Filed: Jan. 13, 2012

(86) PCT No.: PCT/US2012/021311
§ 371 (c)(1),
(2), (4) Date: Sep. 23, 2013

(87) PCT Pub. No.: WO2012/097297
PCT Pub. Date: Jul. 19, 2012

(65) Prior Publication Data
US 2014/0005763 A1    Jan. 2, 2014

Related U.S. Application Data

(60) Provisional application No. 61/432,787, filed on Jan. 14, 2011.

(51) Int. Cl.
*A61N 1/00* (2006.01)
*A61N 1/05* (2006.01)
(Continued)

(52) U.S. Cl.
CPC .......... *A61N 1/0551* (2013.01); *A61F 2/0811* (2013.01); *A61F 2/72* (2013.01); *A61L 27/34* (2013.01); *A61L 2430/32* (2013.01)

(58) Field of Classification Search
CPC ................................. A61N 1/05; A61N 1/056
(Continued)

(56) References Cited

U.S. PATENT DOCUMENTS

| 4,341,221 A | 7/1982 | Testerman |
| 4,585,652 A | 4/1986 | Miller et al. |

(Continued)

FOREIGN PATENT DOCUMENTS

| WO | 97/16545 A1 | 5/1997 |
| WO | 2007/028003 A2 | 3/2007 |

(Continued)

OTHER PUBLICATIONS

Peramo, Antonio, et al., "In Situ Polymerization of a Conductive Polymer in Acellular Muscle Tissue Constructs," Tissue Engineering: Part A, vol. 14, No. 3, pp. 423-432 (2008).

(Continued)

*Primary Examiner* — Nadia A Mahmood
(74) *Attorney, Agent, or Firm* — Harness, Dickey & Pierce, P.L.C.

(57) ABSTRACT

The present disclosure provides a regenerative peripheral nerve interface (RPNI) for a subject comprising an insulating substrate, at least one metallic electrode deposited onto the insulating substrate forming a thin-film array; a portion of the at least one metallic electrode surface having a layer of a first conductive polymer and a layer of decellularized small intestinal submucosa (SIS) coating a portion of the electrode, wherein a second conductive polymer is electrochemically polymerized through the SIS to form the regenerative peripheral nerve interface. The present disclosure also provides that a layer of muscle tissue contacts the regenerative peripheral nerve interface.

23 Claims, 17 Drawing Sheets

(51) Int. Cl.
    *A61F 2/72* (2006.01)
    *A61L 27/34* (2006.01)
    *A61F 2/08* (2006.01)

(58) Field of Classification Search
    USPC .............................................. 607/2, 116, 118
    See application file for complete search history.

(56) References Cited

U.S. PATENT DOCUMENTS

| | | | |
|---|---|---|---|
| 4,662,884 | A | 5/1987 | Stensaas et al. |
| 5,031,621 | A | 7/1991 | Grandjean et al. |
| 5,092,332 | A | 3/1992 | Lee et al. |
| 5,130,412 | A | 7/1992 | Wellinghoff et al. |
| 5,368,028 | A | 11/1994 | Palti |
| 5,513,636 | A | 5/1996 | Palti |
| 5,540,734 | A | 7/1996 | Zabara |
| 6,095,148 | A | 8/2000 | Shastri et al. |
| 6,132,752 | A | 10/2000 | Pickett et al. |
| 6,179,835 | B1 | 1/2001 | Panescu et al. |
| 6,190,893 | B1 | 2/2001 | Shastri et al. |
| 6,197,881 | B1 | 3/2001 | Cosnier |
| 6,294,245 | B1 | 9/2001 | Roitman et al. |
| 6,331,244 | B1 | 12/2001 | Lewis et al. |
| 6,448,076 | B2 | 9/2002 | Dennis et al. |
| 6,468,304 | B1 | 10/2002 | Dubois-Rande et al. |
| 6,569,654 | B2 | 5/2003 | Shastri et al. |
| 6,627,154 | B1 | 9/2003 | Goodman et al. |
| 6,696,575 | B2 | 2/2004 | Schmidt et al. |
| 6,730,212 | B1 | 5/2004 | Yamagishi et al. |
| 6,890,715 | B1 | 5/2005 | Lewis et al. |
| 7,045,205 | B1 | 5/2006 | Sager |
| 7,070,592 | B2 | 7/2006 | Santini, Jr. et al. |
| 7,120,486 | B2 | 10/2006 | Leuthardt et al. |
| 7,147,865 | B2 | 12/2006 | Fishman et al. |
| 7,181,288 | B1 | 2/2007 | Rezai et al. |
| 7,233,097 | B2 | 6/2007 | Rosenthal et al. |
| 7,708,908 | B2 | 5/2010 | Kim et al. |
| 8,005,526 | B2 | 8/2011 | Martin et al. |
| 8,180,461 | B2 | 5/2012 | Mamo et al. |
| 8,353,897 | B2 | 1/2013 | Doyle et al. |
| 8,936,794 | B2 | 1/2015 | Martin et al. |
| 9,044,347 | B2 | 6/2015 | Cederna et al. |
| 9,352,146 | B2 | 5/2016 | Langhals et al. |
| 2005/0033132 | A1 | 2/2005 | Shults et al. |
| 2005/0048651 | A1 | 3/2005 | Ryttsen et al. |
| 2005/0121068 | A1 | 6/2005 | Sager et al. |
| 2005/0234513 | A1 | 10/2005 | Alexander et al. |
| 2005/0263394 | A1 | 12/2005 | Lewis et al. |
| 2006/0057451 | A1 | 3/2006 | Okuzaki et al. |
| 2006/0160100 | A1 | 7/2006 | Gao et al. |
| 2007/0060815 | A1 | 3/2007 | Martin et al. |
| 2007/0073130 | A1 | 3/2007 | Finch et al. |
| 2008/0097280 | A1 | 4/2008 | Martin et al. |
| 2009/0118806 | A1 | 5/2009 | Vetter et al. |
| 2009/0292325 | A1 | 11/2009 | Cederna et al. |
| 2010/0211172 | A1* | 8/2010 | Bellamkonda ....... A61B 5/0031 623/11.11 |
| 2010/0228335 | A1* | 9/2010 | Schorgl ................ A61L 31/005 623/1.15 |
| 2011/0087315 | A1 | 4/2011 | Richardson-Burns et al. |
| 2011/0257504 | A1 | 10/2011 | Hendricks et al. |
| 2012/0232630 | A1 | 9/2012 | Daneshvar |
| 2013/0304174 | A1 | 11/2013 | Langhals et al. |
| 2014/0005763 | A1 | 1/2014 | Cederna et al. |

FOREIGN PATENT DOCUMENTS

| | | |
|---|---|---|
| WO | 2008/085199 A2 | 7/2008 |
| WO | 2010/011386 A2 | 1/2010 |
| WO | 2011/127166 A2 | 10/2011 |
| WO | 2012/097297 A2 | 7/2012 |

OTHER PUBLICATIONS

Pini, Niccolò, et al., "In situ growth of interdigitated electrodes made of polypyrrole for active fiber composites," Polymers for Advanced Technologies, vol. 18, pp. 249-253 (Mar. 2007) (published online Feb. 1, 2007).

Smela, Elisabeth, "Conjugated Polymer Actuators for Biomedical Applications," Advanced Materials, vol. 15, No. 6, pp. 481-494 (Mar. 17, 2003).

Spinks, Geoffrey M., et al., "Actuation behaviour of layered composites of polyaniline, carbon nanotubes and polypyrrole," Synthetic Metals, vol. 151, pp. 85-91 (2005) (published online Jun. 13, 2005).

Talbi, H., et al., "Electropolymerization of aniline on carbonized polyacrylonitrile aerogel electrodes: applications for supercapacitors," Journal of Applied Electrochemistry, vol. 33, pp. 465-473 (2003).

Urbanchek, M.G., et al., "A Tissue-Based Bioelectrical Interface With Reduced Impedance Compared to Copper Wire and Nerve," 54th Annual Meeting, Plastic Surgery Research Council, May 27-30, 2009, Pittsburgh, PA, PSRC Abstract Supplement, vol. 126, No. 3 (Supplement), p. 26 (Jun. 2009) (Abstract only).

Urbanchek, M.G., et al., "Myoblast and Nerve Compatibility with PEDOT an Intrinsically Conductive Material," American Society of Plastic Surgeons Meeting, Nov. 2008, Chicago, IL (Presentation).

Urbanchek, M.G., et al., "Nerve Regeneration Through an Electrically Conducting Polymer Nerve Graft," 54th Annual Meeting, Plastic Surgery Research Council, May 27-30, 2009, Pittsburgh, PA, PSRC Abstract Supplement, vol. 126, No. 3 (Supplement), p. 90 (Jun. 2009) (Abstract only).

Watt, A.A.R., et al., "A PbS quantum-cube: conducting polymer composite for photovoltaic applications," Current Applied Physics, vol. 4, pp. 320-322 (2004).

Kim, Dong-Hwan, "Effect of Immobilized Nerve Growth Factor on Conductive Polymers: Electrical Properties and Cellular Response," Advanced Functional Materials, vol. 17, pp. 79-86 (2007) (published online Nov. 20, 2006).

Jadcherla, Yamini, et al., "Nerve Regeneration through PEDOT, an Electrically Conducting Polymer Nerve Graft," Plastic and Reconstructive Surgery, vol. 124, No. 4 Supplement, p. 67 (Oct. 2009).

International Preliminary Report on Patentability dated Jul. 16, 2013 for PCT International Application No. PCT/US2012/021311 (Pub. No. WO 2012/097297).

International Preliminary Report on Patentability dated Nov. 2, 2010 for PCT International Application No. PCT/US2009/042342 (Pub. No. WO 2010/011386).

Lock, John P., et al., "Electrochemical investigation of PEDOT films deposited via CVD for electrochromic applications," Synthetic Metals, vol. 157, pp. 894-898 (2007) (published online Oct. 29, 2007).

Abidian, M.R., et al., "Sensory Protection Recovery Follows Nerve Regeneration Through an Electrically Conducting Nerve Graft," 54th Annual Meeting, Plastic Surgery Research Council, May 27-30, 2009, Pittsburgh, PA, PSRC Abstract Supplement, vol. 126, No. 3 (Supplement), p. 40 (Jun. 2009) (Abstract only).

Aszmann, Oskar C., et al., "Evidence in Support of Collateral Sprouting After Sensory Nerve Resection," Annals of Plastic Surgery, vol. 37, No. 5, pp. 520-525 (1996).

Aszmann, Oskar C., et al., "Neuroma Prevention by End-to-Side Neurorraphy: An Experimental Study in Rats," Journal of Hand Surgery, vol. 28A, No. 6, pp. 1022-1028 (Nov. 2003).

Chandra, S., et al., "Proton-conducting gel electrolyte," Solid State Ionics, vol. 154-155, pp. 609-619 (2002).

Lebedev, Mikhail, et al., "Brain-machine interfaces: past, present and future," TRENDS in Neurosciences, vol. 29, No. 9, pp. 536-546 (2006) (published online Jul. 21, 2006).

Egeland, B.M., et al., "Biosynthetic Poly(3,4-ethylenedioxythiophene) (PEDOT) PNS Interfaces Can Deliver Afferent SNAPs With High Efficiency," American Society of Plastic Surgeons Meeting, Oct. 30-Nov. 6, 2008, Chicago, IL (Summary).

Egeland, Brent M., et al., "In Vivo Electrical Conductivity across Critical Nerve Gaps Using Poly(3,4-ethylene-dioxythiophene)-Coated Neural Interfaces," Plastic and Reconstructive Surgery, vol. 126, No. 6, pp. 1865-1873 (Dec. 2010).

(56) References Cited

OTHER PUBLICATIONS

Egeland, B.M., et al., "Biosynthetic Poly(3,4-ethylenedioxythiophene) (PEDOT) PNS Interfaces Can Deliver Afferent SNAPs With High Efficiency," American Society for Peripheral Nerve Annual Scientific Meeting, Maui, HI, Jan. 11, 2009 (also presented at Annual Research Conference, Ann Arbor, MI, Mar. 2009) (Presentation).
Egeland, Brent, et al., "In Vivo Electrophysiologic Properties of Poly 3,4-ethylene-dioxythiophene (PEDOT) in a Biosynthetic Nerve Interface," Midwestern Association of Plastic Surgeons, 48th Annual Scientific Meeting, May 4, 2008, Chicago, IL (Abstract and Presentation).
Egeland, Brent M., et al., "Poly(3,4-ethylenedioxythiophene) PEDOT Bioengineered Constructs Can Deliver Afferent SNAPs With High Efficiency," American Society of Peripheral Nerve Annual Meeting, Jan. 6-9, 2009, Maui, HI (Presentation).
Egert, Daniel, et al., "New Class of Chronic Recording Multichannel Neural Probes With Post-Implant Self-Deployed Satellite Recording Sites," Solid-State Sensors, Actuators and Microsystems Conference (TRANSDUCERS), Proceedings from IEEE 16th International Conference, Jun. 5-9, 2011, pp. 958-961.
Gao, Mei, et al., "Biosensors Based on Aligned Carbon Nanotubes Coated with Inherently Conducting Polymers," Electroanalysis, vol. 15, No. 13, pp. 1089-1094 (2003).
Herr, Hugh, "New Horizons for Orthotic & Prosthetic Technology," Materials Research Society Spring Meeting, Symposium U: Advanced Materials for Neuroprosthetic Interfaces, Session U9: Integrated Designs and Devices, Apr. 12, 2007, San Francisco, CA (Oral Presentation) (Abstract only).
International Search Report and Written Opinion of the ISA for PCT/US2012/021311, ISA/KR, dated Aug. 29, 2012.
International Search Report for PCT/US2009/042342, ISA/KR, dated Feb. 5, 2010.
Supplementary European Search Report in European Patent Application No. 06824877.2, a national phase of PCT/US2006034199, dated Mar. 9, 2010.
Abidian, M.R., et al., "Conducting-Polymer Nanotubes for Controlled Drug Release," (2006), Advanced Materials, 18, pp. 405-409.
Abidian, M.R., et al., Experimental and Theoretical Characterization of Implantable Neural Microelectrodes Modified with Conducting Polymer Nanotubes, Biomaterials, vol. 29, 2008 (available online Dec. 18, 2007), pp. 1273-1283.
Baghmanli, Ziya et al., "Impact of PEDOT on Peripheral Nerve Regeneration and Muscle Reinnervation," Plastic and Reconstructive Surgery, 70A, p. 52 (Jun. 2010 supplement).
Campbell, T.E., et al., "Incorporation of Erythrocytes into Polypyrrole to Form the Basis of a Biosensor to Screen for Rhesus (D) Blood Groups and Rhesus (D) Antibodies," (1999), Electroanalysis, vol. 11, No. 4, pp. 215-222.
Chew, S.Y., et al., "Sustained Release of Proteins from Electrospun Biodegradable Fibers," (2005), Biomacromolecules, 6, pp. 2017-2024.
Cui, et al., "Surface modification of neural recording electrodes with conducting polymer/biomolecule blends," (2001), J. Biomed. Mater. Res., vol. 56A, No. 2, pp. 261-272.
Cui, X., et al., "Electrochemical deposition and characterization of conducting polymer polypyrrole/PSS on multichannel neural probes," (2001), Sensors and Actuators A, 93, pp. 8-18.
Cui, X., et al., "Electrochemical deposition and characterization of poly(3,4-ethylenedioxythiophene) on neural microelectrode arrays," (2003), Sensors and Actuators B, 89, pp. 92-102.
Cui, X., et al., "In vivo studies of polypyrrole/peptide coated neural probes," (2003), Biomaterials, 24, pp. 777-787.
DiPaolo, B.C., et al., "Nanofiber scaffolding for improved neural electrode biocompatability," (2003), IEEE 29th Annual Conference, pp. 21-22.
Dong, H., et al., "Sub-micrometer Conducting Polyaniline Tubes Prepared from Polymer Fiber Templates," (2004), Chem. Mater., 16, pp. 371-373.
Ghosh, S., et al., "Electrochemical Characterization of Poly(3,4-ethylene dioxythiophene) Based Conducting Hydrogel Networks," (2000) Journal of the Electrochemical Society, vol. 147, No. 5, pp. 1872-1877.
Gilmore, K., et al., "Preparation of Hydrogel/Conducting Polymer Composites," (1994), Polymer Gels and Networks, 2, pp. 135-143.
Gooding, J.J., et al., "Electrochemical modulation of antigen-antibody binding," (2004), Biosensors and Bioelectronics, 20, pp. 260-268.
Heiduschka, P. et al., "Implantable Bioelectronic Interfaces for Lost Nerve Functions," Progress in Neurobiology, 1998, vol. 55, pp. 433-461.
Khor, E., et al., "In situ polymerization of pyrrole in animal tissue in the formation of hybrid biomaterials," (1995), Biomaterials, vol. 16, No. 8, pp. 657-661.
Kim, B.C., et al., "Electroformation of conducting polymers in a hydrogel support matrix," (2000), Polymer, 41, pp. 1783-1790.
Kim, B.H., et al., "Synthesis, characteristics, and field emission of doped and de-doped polypyrrole, polyaniline, poly(3,4-ethylenedioxythiophene) nanotubes and nanowires," (2005), Synthetic Metals, 150, pp. 279-284.
Kim, D., et al., "Conducting polymers grown in hydrogel scaffolds coated on neural prosthetic devices," (2004), J.Biomed. Mater. Res., 71A(4), pp. 577-585.
Kim K., et al., "Incorporation and controlled release of a hydrophilic antibiotic using poly(lactide-co-glycolide)-based electrospun nanofibrous scaffolds," (2004), Journal of Controlled Release, 98, pp. 47-56.
Kipke, D. R., et al., "Silicon-Substrate Intracortical Microelectrode Arrays for Long-Term Recording of Neuronal Spike Activity in Cerebral Cortex," (2003), IEEE Transactions on Neural Systems and Rehabilitation Engineering, vol. 11, No. 2, pp. 151-155.
Kositsky, M., et al., "Dynamical Dimension of a Hybrid Neurorobotic System," (2003), IEEE Transactions on Neural Systems and Rehabilitation Engineering, vol. 11, No. 2, pp. 155-159.
Murji, A., et al., "The Role of Intraoperative Frozen Section Histology in Obstetrical Brachial Plexus Reconstruction", J. Reconstr. Microsurg, 2008. 24(3): p. 203-209.
Nyberg, T., et al., Ion Conducting Polymer Microelectrodes for Interfacing with Neural Networks, Journal of Neuroscience Methods, vol. 160, 2007, pp. 16-25 (abstract only).
Nyberg, T., et al., "Polymer Hydrogel Microelectrodes for Neural Communication," (2002), Biomedical Microdevices vol. 4, No. 1, pp. 43-52.
Rahman, Md. Aminur et al., "The biosensor based on the pyruvate oxidase modified conducting polymer for phosphate ions determinations," (2006) Biosensors & Bioelectronics, vol. 21, No. 7, pp. 1116-1124 (Article in Press version and publication information provided).
Richardson-Burns, Sarah M. et al., "Electrochemical polymerization of conducting polymers in living neural tissue", J. Neural Eng. 4 (2007), L6-L13.
Richardson-Burns, Sarah M. et al., "Polymerization of the conducting polymer poly(3,4-ethylenedioxythiophene) (PEDOT) around living neural cells", Biomaterials, vol. 28, 2007, pp. 1539-1552.
Schmidt, C.E., et al., "Stimulation of neurite outgrowth using an electrically conducting polymer," (Aug. 1997), Applied Biological Sciences: Proc. Natl. Acad. Sci. USA, vol. 94, pp. 8948-8953.
Woerly, S., "Restorative surgery of the central nervous system by means of tissue engineering using NeuroGel implants," (2000), Neurosurg. Rev., 23, pp. 59-77.
Xiao, Y., et al., "Electrochemical polymerization of poly(hydroxymethylated-3,4-ethylenedioxythiophene) (PEDOT-MeOH) on multichannel neural probes," (2004), Sensors and Actuators B, 99, pp. 437-443.
Yang, J., et al., "Microporous conducting polymers on neural microelectrode arrays II. Physical characterization," (2004), Sensors and Actuators A, 113, pp. 204-211.
Yang, J., et al., "Microporous conducting polymers on neural microelectrode arrays I Electrochemical deposition," (2004), Sensors and Actuators B, 101, pp. 133-142.

(56) References Cited

OTHER PUBLICATIONS

Yang, J., et al., "Ordered surfactant-templated poly(3,4-ethylenedioxythiophene) (PEDOT) conducting polymer on microfabricated neural probes," (2005), Acta Biomaterialia, 1, pp. 125-136.

Zhang, Y., et al., "Recent development of polymer nanofibers for biomedical and biotechnological applications," (2005), Journal of Materials Science: Materials in Medicine, 16, pp. 933-946.

* cited by examiner

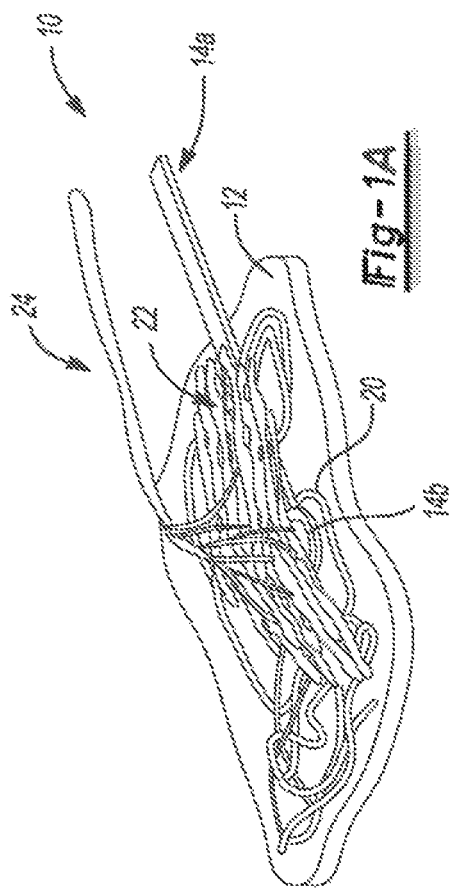
*Fig-1A*
*Fig-1B*
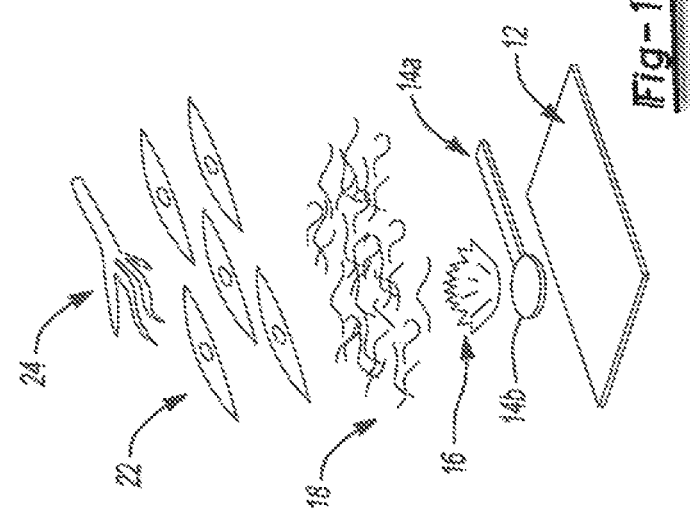
*Fig-1C*

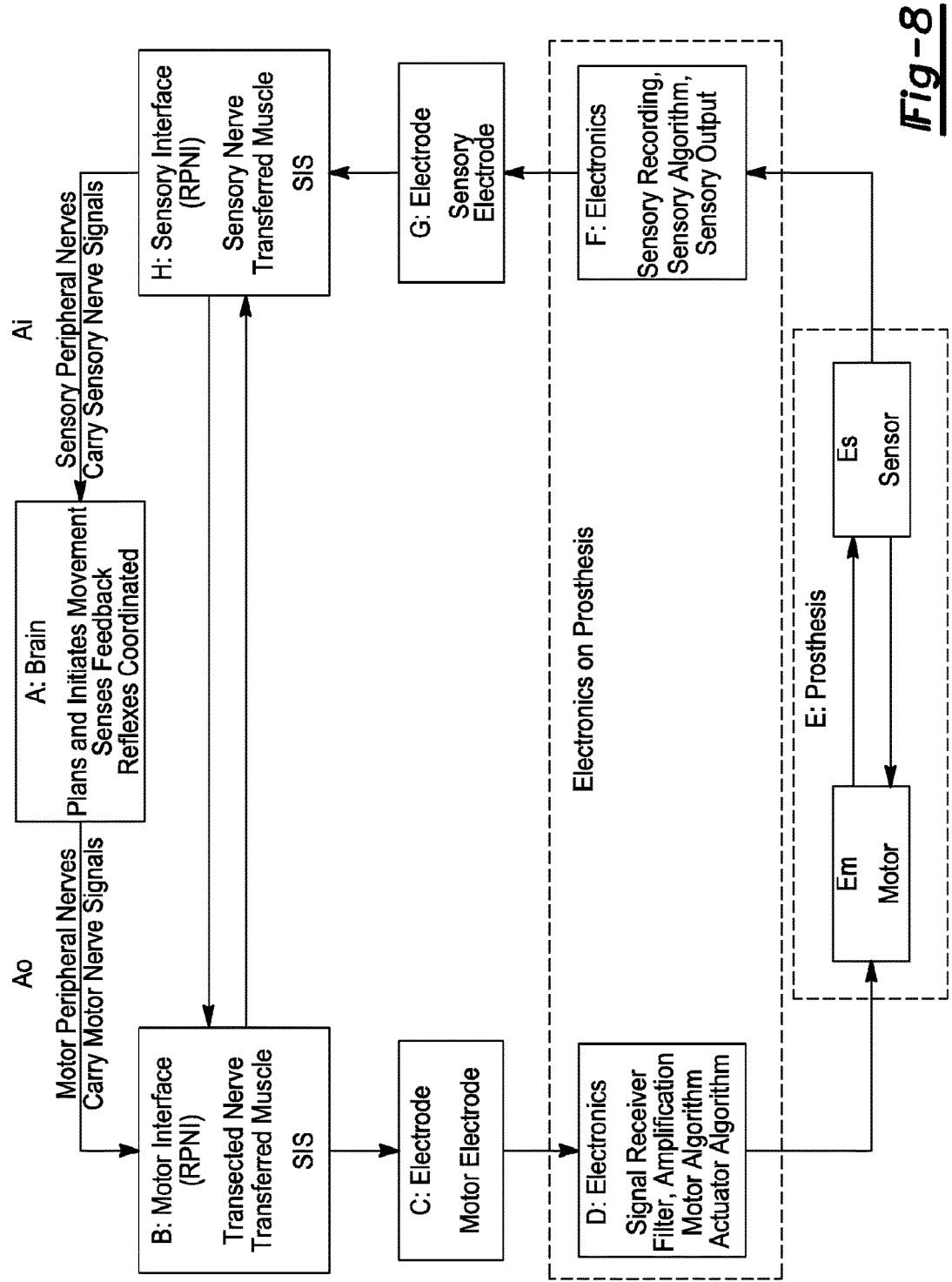

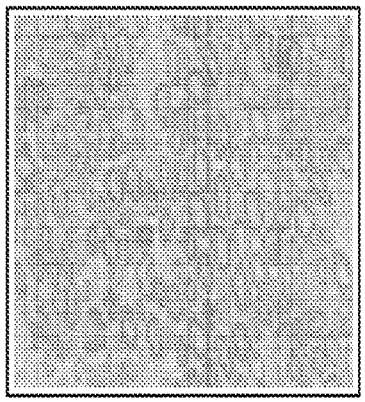
Fig-9A A. Sham
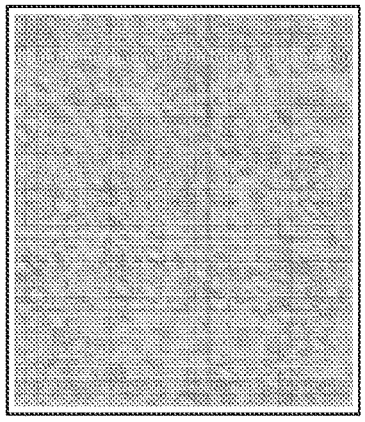
Fig-9B B. Autograft
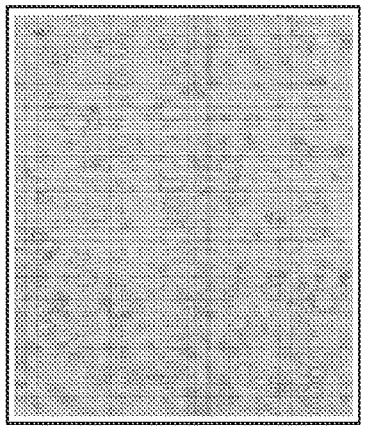
Fig-9C C. Decellular Nerve
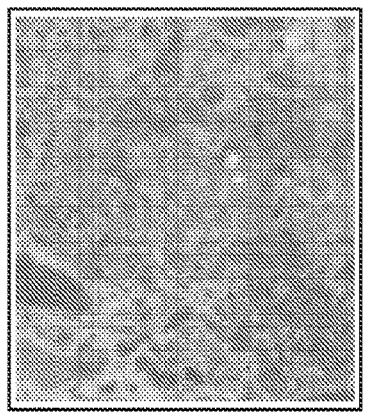
Fig-9D D. Dry PEDOT
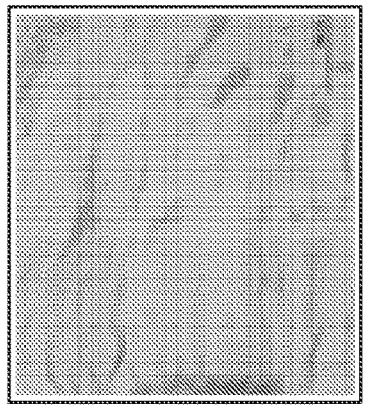
Fig-9E E. Wet PEDOT
Fig-9F F. No Graft

REGENERATIVE PERIPHERAL NERVE INTERFACE

CROSS-REFERENCE TO RELATED APPLICATIONS

This application is a National Stage of International Application No. PCT/US2012/021311 filed on Jan. 13, 2012 and published as WO2012/697297 on Jul. 19, 2012, and claims the benefit and priority of U.S. Patent Application No. 61/432,787 filed on Jan. 14, 2011. The entire disclosures of each the above applications are incorporated herein by reference.

GOVERNMENT RIGHTS

This invention was made with government support under W911NF-06-1-0218 awarded by the Army/ARO and N66001-11-C-4190 awarded by the Navy/SPAWAR. The Government has certain rights in the invention.

FIELD

The present technology relates to a regenerative peripheral nerve interface, including methods and devices relating to regenerative peripheral nerve interfaces.

INTRODUCTION

This section provides background information related to the present disclosure which is not necessarily prior art.

Statistics estimate there are about 1.7 million people in the US alone living with limb loss. This corresponds to about 1 in every 200 people. There is a need to create reliable neural interfaces that can seamlessly and naturally connect patients with artificial arms and legs. The peripheral nerve system is viewed as the ideal location for multiple motor and sensory interfaces for closed-loop neural control of high fidelity prosthetic devices. The peripheral nerves contain sorted brain signals for fine motor control and sensory feedback, are closest to the prosthesis, and are safely and easily accessible for surgery.

Over 40,000 Americans undergo major upper extremity amputations annually, a figure that continues to rise in the wake of ongoing military conflicts. Despite growing demand, however, today's body-powered prosthetics are still based on 19$^{th}$ century technology. While modern robotic technology has produced prosthetics capable of replicating complex movement and sensing environmental stimuli on par with the human arm, interfacing these machines with living tissues has proved challenging.

Current-generation neural interfaces that control prosthetic devices show promise early on, but signal degradation and failure gradually occur from scarring, inflammation, and axonal pruning. In the acute phase, edema, hemorrhage, and axonal damage threaten the fidelity of the device. In the chronic phase, macrophage and fibroblast responses result in robust scarring which causes signal loss and interface failure. Following trauma, divided peripheral nerves have an impressive ability to regenerate and sprout nerve fibers in search of new neural targets. In the nerve stumps of amputated limbs, however, this capability makes it possible for sprouting nerve fibers to form tiny clusters of disorganized nerve fibers known as a neuroma. This detrimental response at the proximal end of a divided peripheral nerve can be a source of pain for the patient as well as a source of signal interference when decoding action potentials.

Electrodes are used in interface designs because they provide high fidelity signaling to the peripheral nerve and attempt to reduce problems at the interface between the electrode and the living tissue. Metallic components are highly conductive and easy to fabricate, but have an unfavorable biocompatibility profile. The mechanical stiffness of these components, mated with the soft surfaces of biologic tissues at the biotic-abiotic interface, likely exacerbates scar formation, which can cause signal interference and nerve damage.

SUMMARY

In various aspects, the present disclosure provides a regenerative peripheral nerve interface (RPNI) for a subject comprising an insulating substrate and at least one metallic electrode disposed on or formed in the insulating substrate. Together the insulating substrate and at least one metallic electrode form a thin-film array. Furthermore, a portion of a surface of at least one metallic electrode has a layer of a first conductive polymer. A portion of the surface has a layer of decellularized small intestinal submucosa (SIS) coating the at least one metallic electrode. A second conductive polymer is electrochemically polymerized through the SIS coating to form the regenerative peripheral nerve interface. In various aspects, such a regenerative peripheral nerve interface is capable of interfacing with tissue in a subject. In certain aspects, the regenerative peripheral nerve interface is encapsulated with a layer of muscle tissue in contact with the SIS coating. Thus in certain aspects, the regenerative peripheral interface is capable of being implanted on at least one nerve ending of the peripheral nerve of the subject. In other aspects, the regenerative peripheral interface is capable of connecting with at least one sensor of a prosthetic device. For example, in certain variations, the regenerative peripheral nerve interface is connected to at least one sensor of a prosthetic device in a subject, and the regenerative peripheral nerve interface is capable of controlling the prosthetic device.

In other aspects, the present disclosure provides a method of forming a regenerative peripheral nerve interface, the method comprising forming a regenerative peripheral nerve interface by coating a portion of at least one metallic electrode with an insulating substrate, wherein the insulating substrate defines a thin-film array, depositing a first layer of a conductive polymer onto the portion of the at least one metallic electrode; and coating at least a portion of the at least one metallic electrode with a layer of decellularized submucosa, wherein a second conductive polymer is electrochemically polymerized through the submucosa to form the regenerative peripheral nerve interface.

In yet other aspects, the present disclosure provides an interfacing device for interfacing between a peripheral nerve of a subject and prosthetic device, the interfacing device comprising: an insulating substrate, at least one metallic electrode deposited onto the insulating substrate defining a thin-film array, a portion of the electrode surface having a layer of a first conductive polymer, a layer of decellularized small intestinal submucosa (SIS) coating a portion of the electrode, wherein a second conductive polymer is electrochemically polymerized through the SIS to form a regenerative peripheral nerve interface and a layer of muscle tissue contacting the regenerative peripheral nerve interface.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-1C illustrate a regenerative peripheral nerve interface (RPNI) in accordance with the present disclosure comprising an insulating substrate, electrodes, and conducting polymers deposited onto porous protein scaffolds, free muscle grafts, and motor and sensory peripheral nerves;

FIG. 8 is an exemplary schematic comprising a diagram of a closed-loop neural control of a prosthesis in accordance with certain aspects of the present disclosure;

FIGS. 9A-9F illustrate nerve histology of test groups, sham (FIG. 9A), autograft (FIG. 9B), decellular nerve (FIG. 9C), DryPEDOT (FIG. 9D), WetPEDOT (FIG. 9E), and no graft (FIG. 9F) with 100× magnification;

Figure 10A:
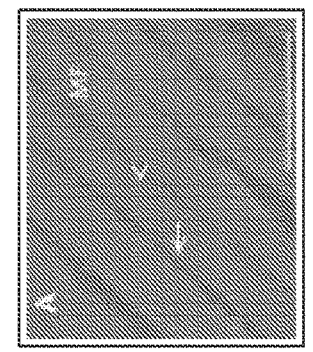
Figure 10B:
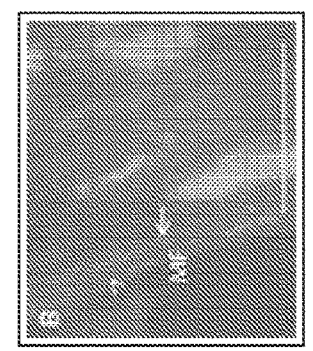
Figure 10C:
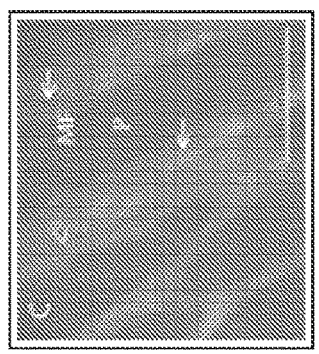
Figure 10D:
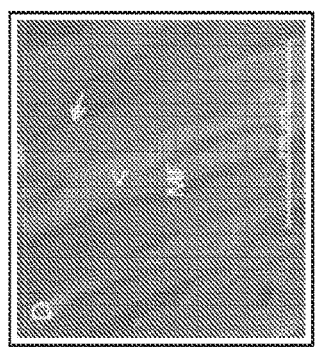
Figure 11A:
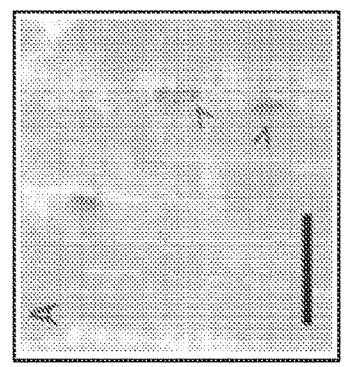
Figure 11B:
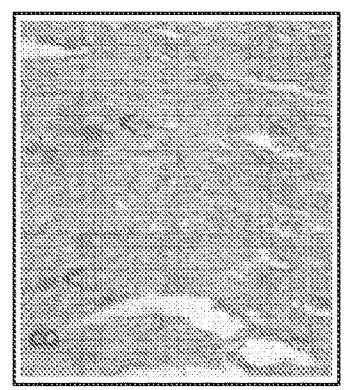
Figure 11C:
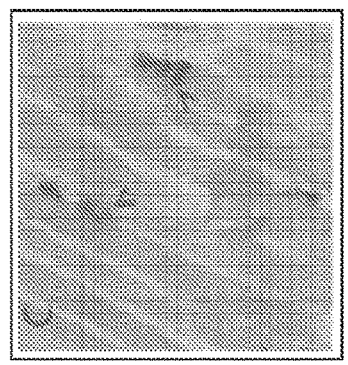
Figure 11D:
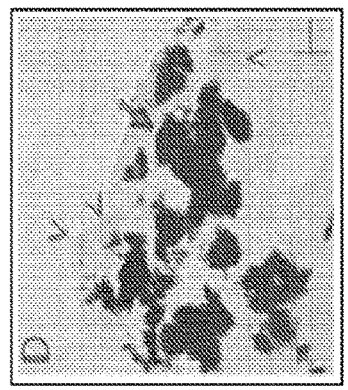

FIGS. 10A-10D illustrate the regenerative peripheral nerve interface (RPNI) prepared in accordance with certain aspects of the present disclosure following 3 to 20 months of implantation. Longitudinal sections from RPNI constructs labeled with fluorescing Anti-Desmin antibody and IgG conjugated-CY3™. FIG. 10A shows a control soleus muscle; FIG. 10B shows maturing myoblasts within RPNI; FIG. 10C shows maturing myoblasts within RPNI containing scaffold chemically polymerized with PEDOT; FIG. 10D shows transferred skeletal muscle within RPNI. Scale bar is 100 μm. Arrow heads indicate fluorescence at muscle Z-lines. Arrows point to muscle nuclei. MF indicates muscle fiber. P indicates scaffold area chemically polymerized with PEDOT;

FIGS. 11A-11D illustrate an RPNI prepared in accordance with certain aspects of the present disclosure following 16 to 20 months of implantation. Longitudinal sections cut from RPNI constructs with purple stained neuromuscular junctions (NMJ) and counterstaining with eosin. FIG. 11A shows control soleus muscle; FIG. 11B shows maturing myoblasts within RPNI; FIG. 11C shows muscle transfer within RPNI; FIG. 11D shows transferred skeletal muscle within RPNI containing scaffold chemically polymerized with PEDOT. Scale bar is 100 μm. Arrow head indicates NMJ. Arrow points to scaffold area chemically polymerized with PEDOT.

Figure 12:
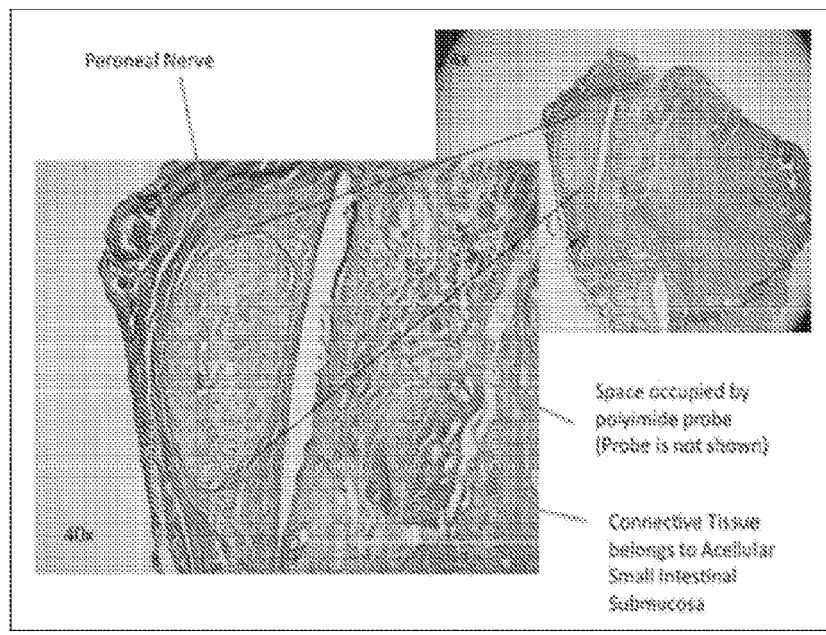
Figure 13:
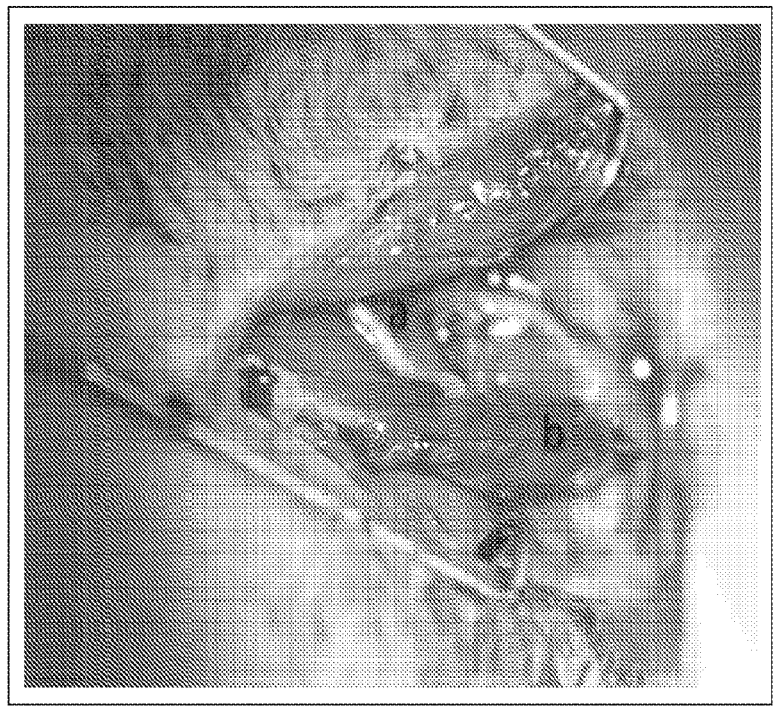
Figure 14:
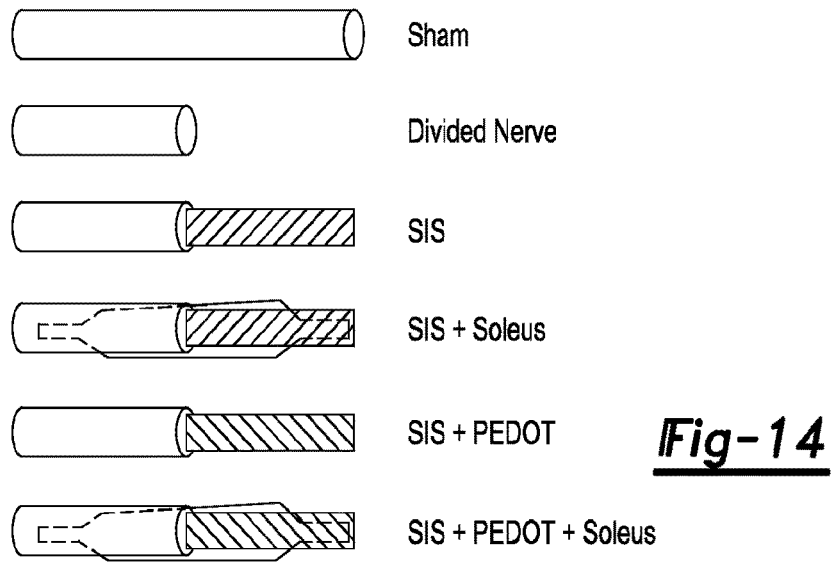
Figure 15:
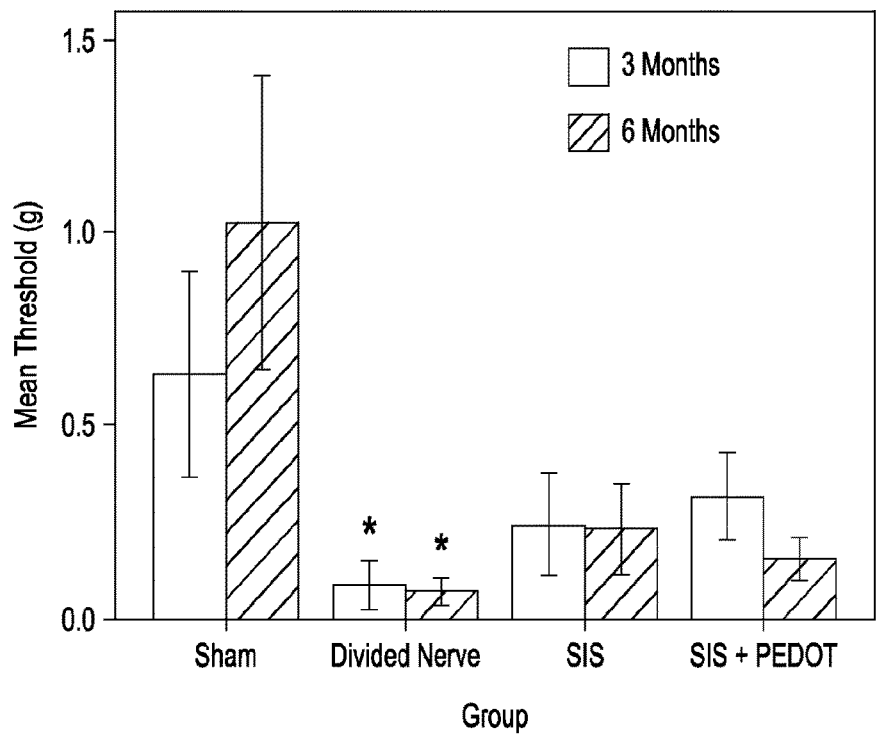
Figure 16:
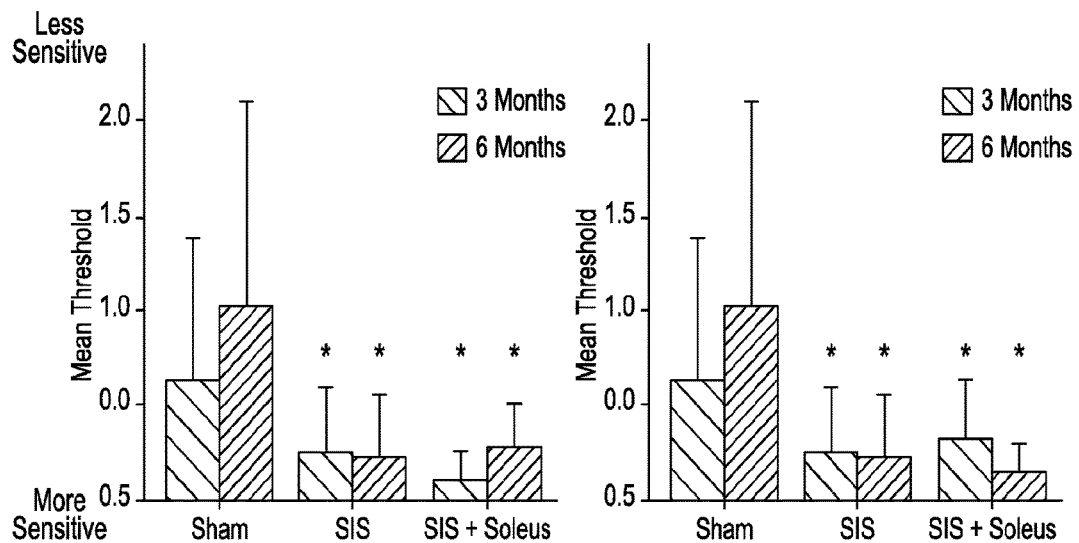
Figure 17:
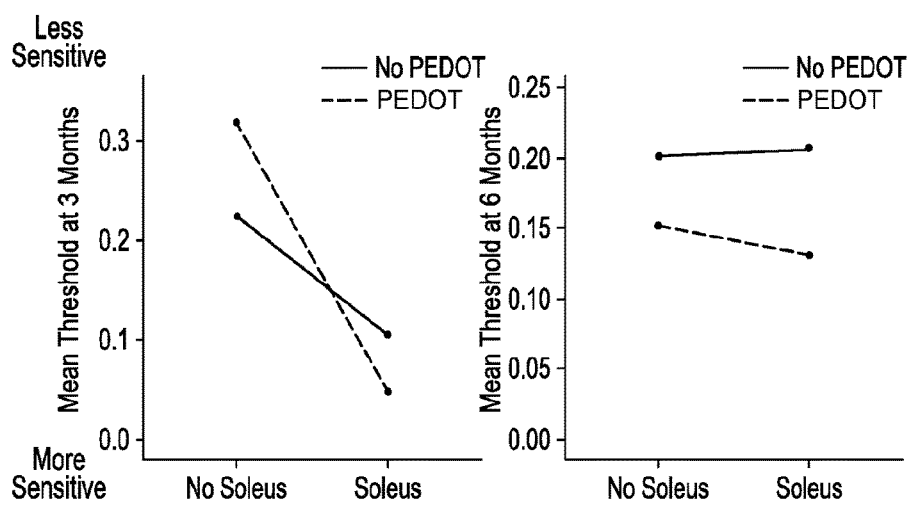
Figure 18A:
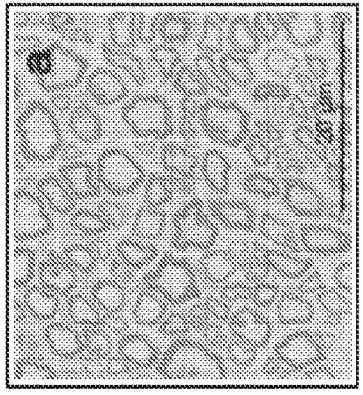
Figure 18B:
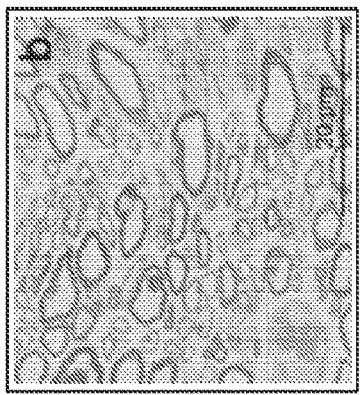
Figure 18C:
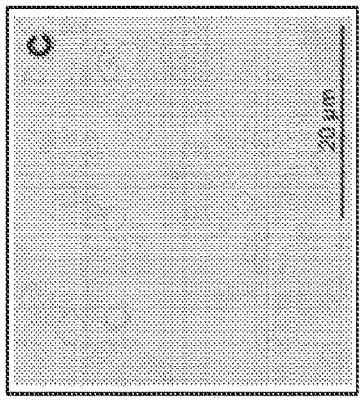
Figure 18D:
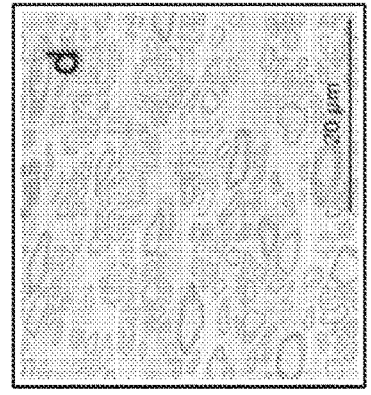
Figure 18E:
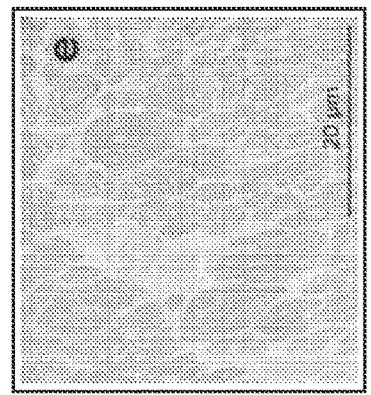
Figure 18F:
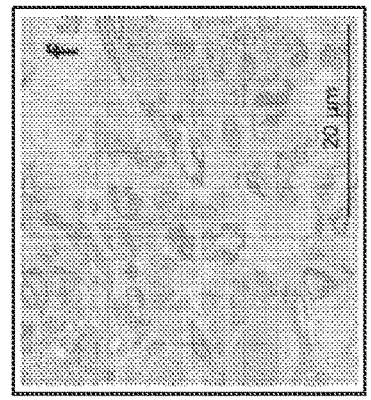
Figure 19:
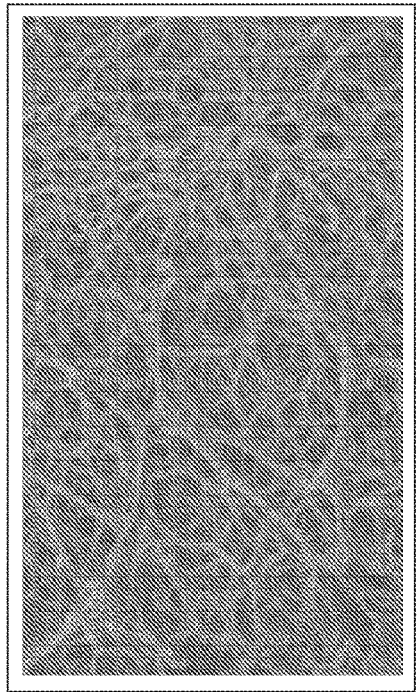
Figure 20:
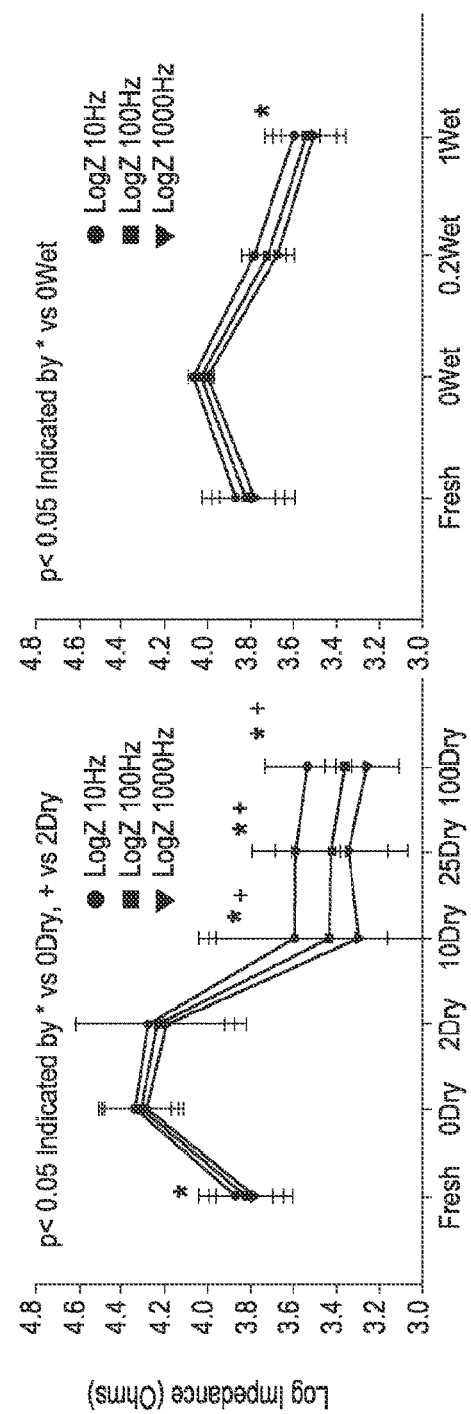
Figures 21, 22:
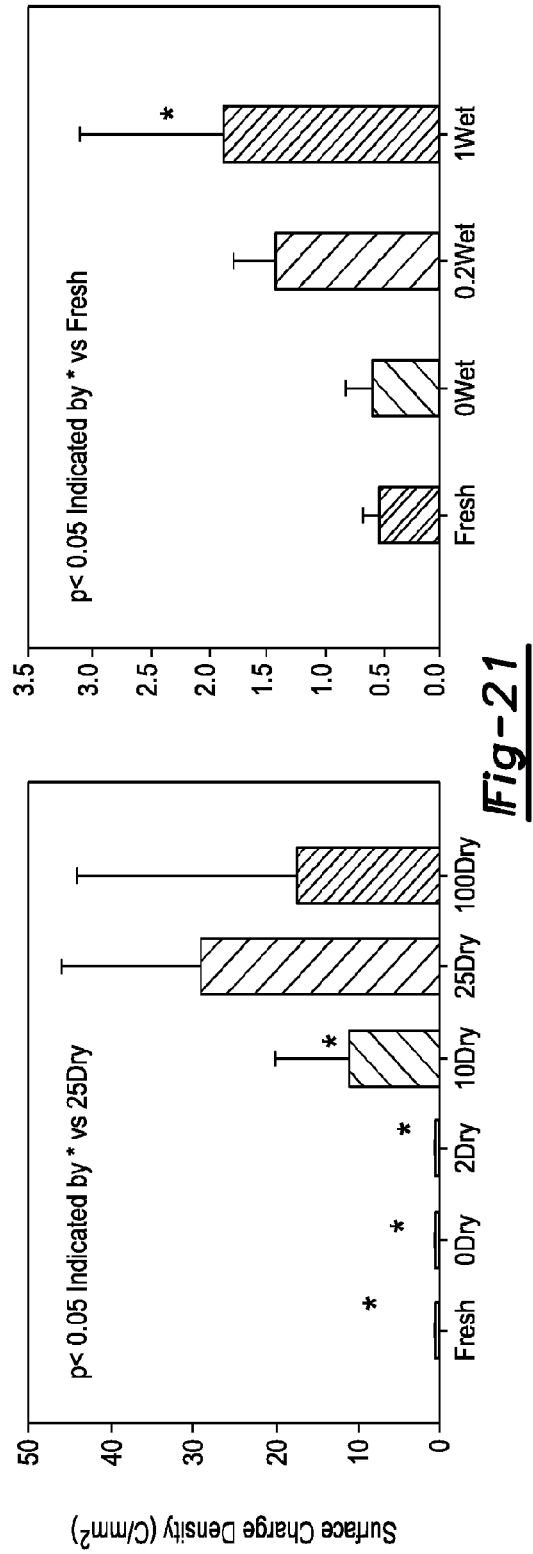
Figure 23:
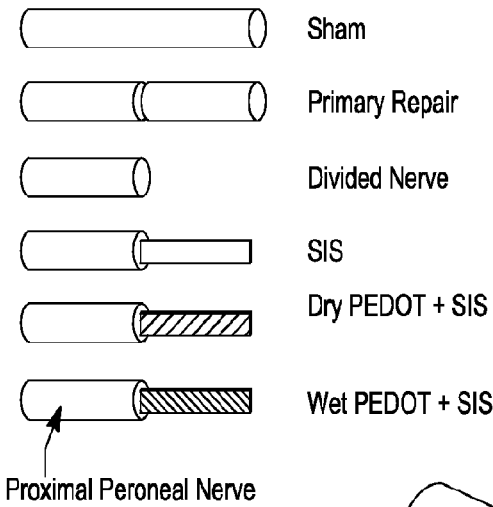
Figure 24:
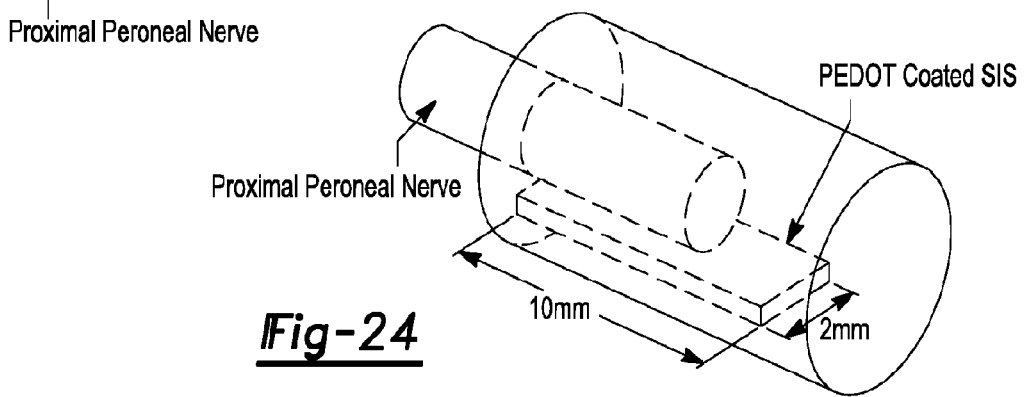
Figure 25:
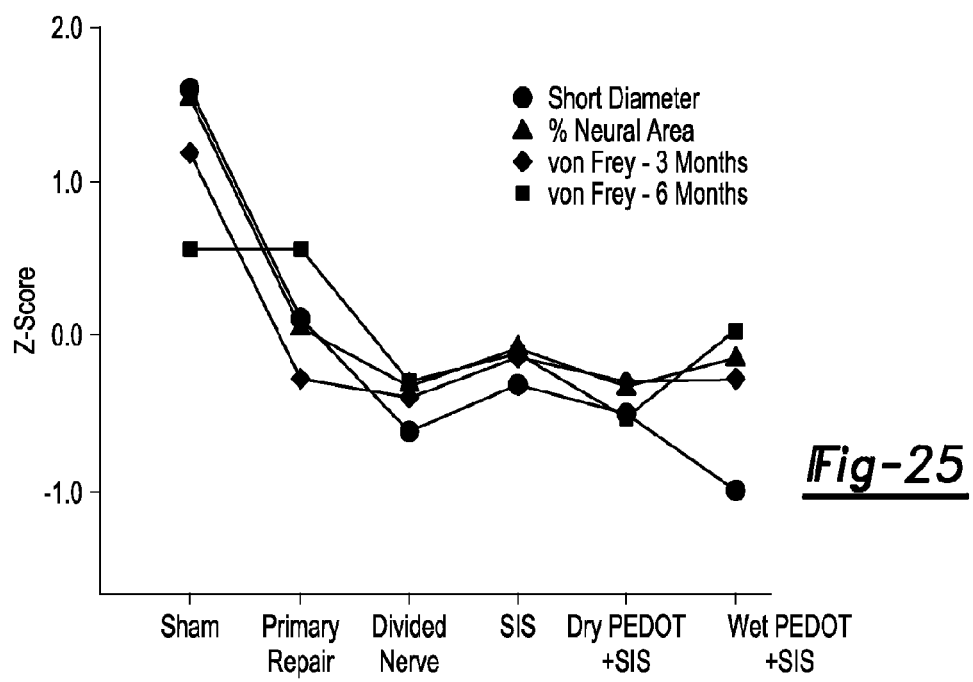
Figure 26B:
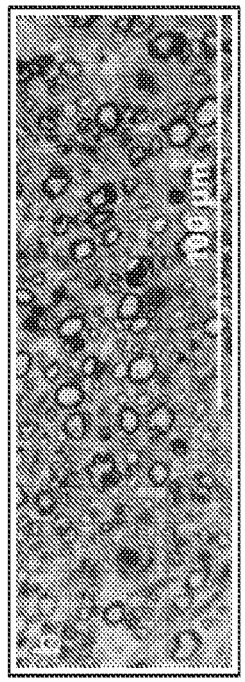
Figure 26D:
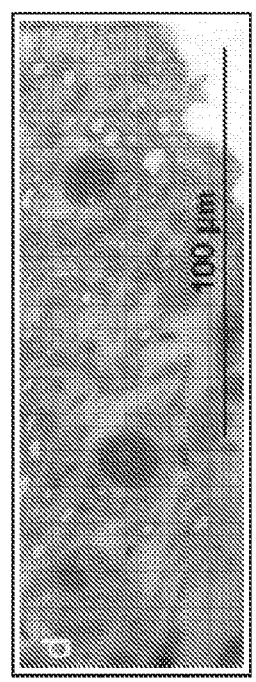
Figure 26F:
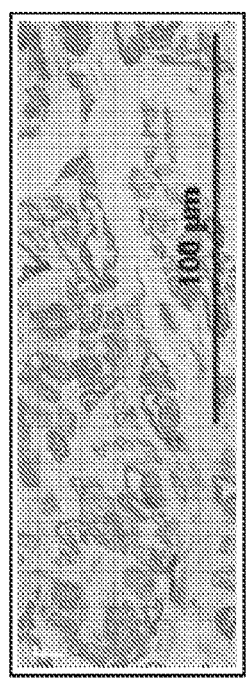
Figure 26A:
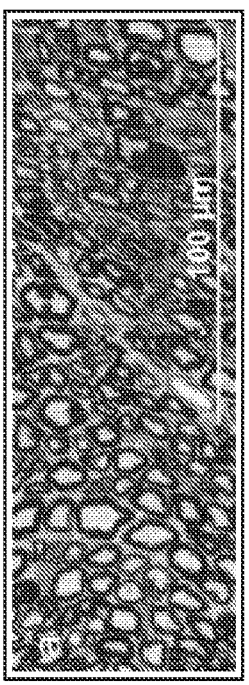
Figure 26C:
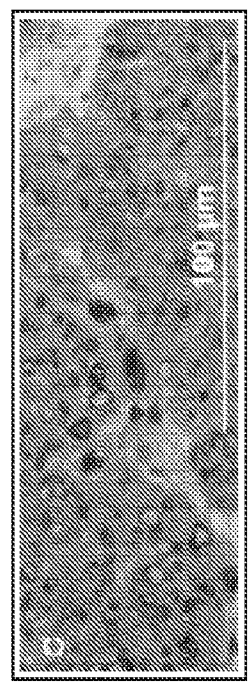
Figure 26E:
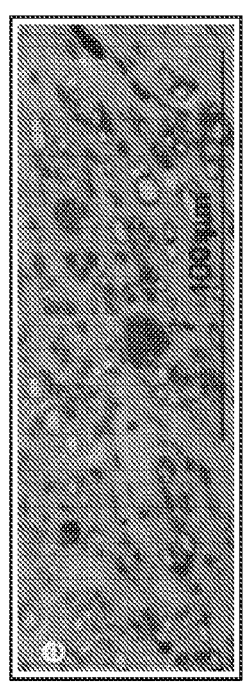
Figure 27A:
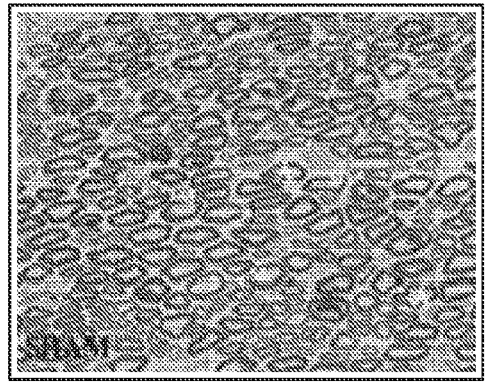
Figure 27B:
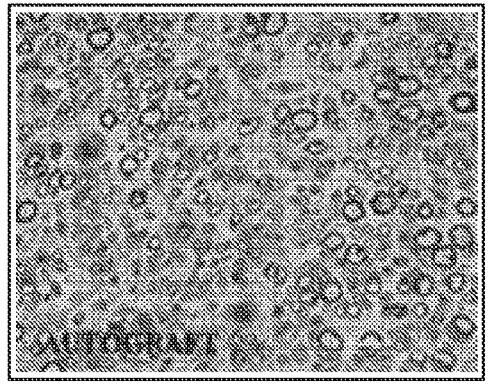
Figure 27C:
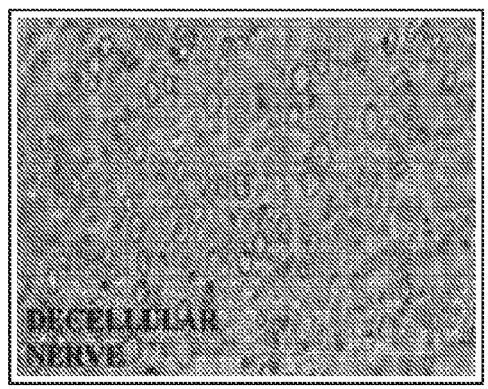
Figure 27D:
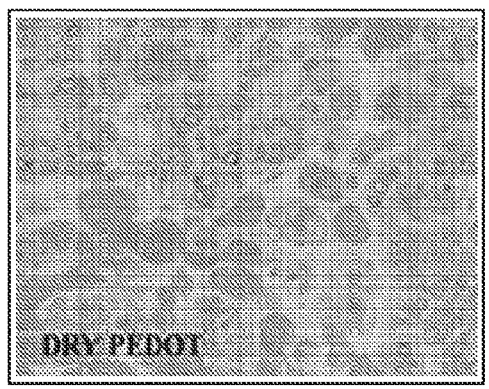
Figure 27E:
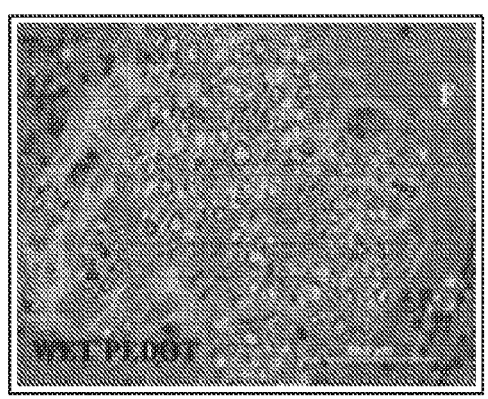
Figure 27F:
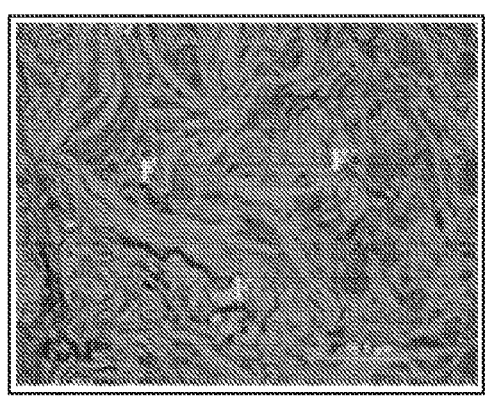
Figure 28:
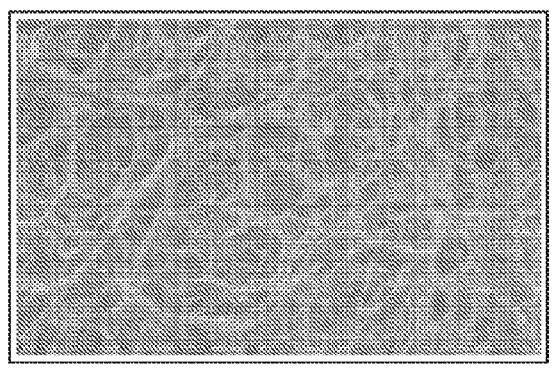
Figure 29:
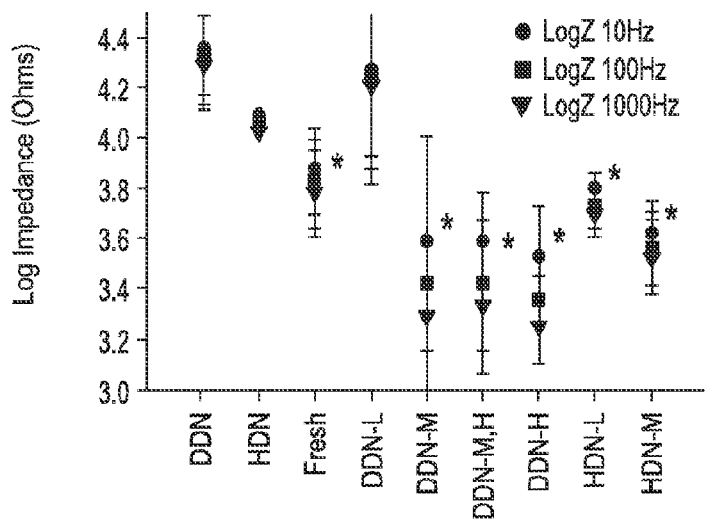
Figure 30:
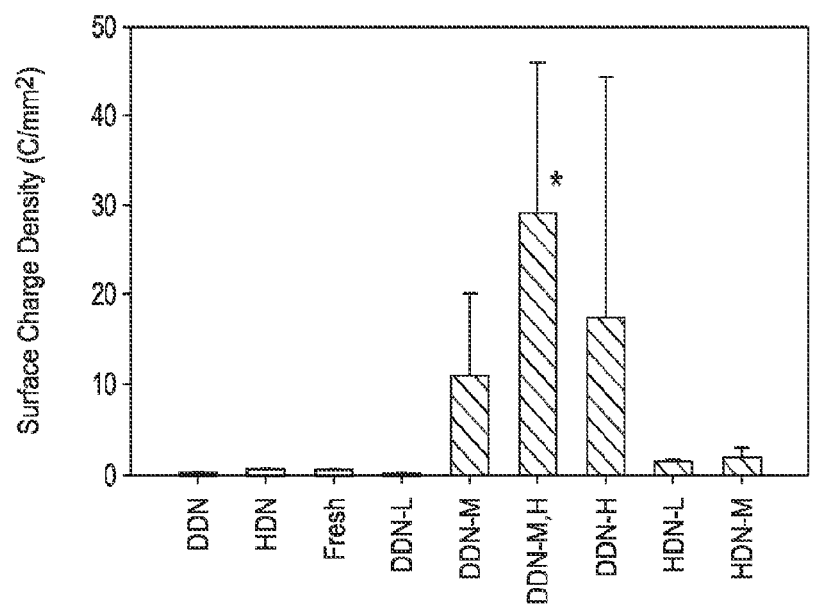

FIG. 12 depicts a peripheral nerve-thin film array hemotoxylen-eosin stained section after 6 weeks. Scale bar is 200 μm;

FIG. 13 depicts a peroneal nerve embedded in soleus free graft wherein a) is the peroneal nerve, and b) is a soleus free graft;

FIG. 14 depicts six groups in a rat peroneal nerve transection model;

FIG. 15 depicts three and six month tactile sensitivity thresholds (g) to von Frey monofilament stimulation. *: more sensitive than Sham, $p<0.05$;

FIG. 16 depicts a tactile sensitivity at 3 and 6 Months. Lower bars indicate greater sensitivity. *Different than sham, $\alpha<0.06$;

FIG. 17 depicts a PEDOT and soleus interactions in tactile sensitivity. Lower values indicate greater sensitivity;

FIG. 18A-18F depicts a representative histology of groups at 6 months. Toluidine blue-stained nerve cross sections from: Sham (FIG. 18A), primary repair (FIG. 18B), divided nerve (FIG. 18C), 4) divided nerve+SIS (FIG. 18D), 5) divided nerve+Dry PEDOT–SIS (FIG. 18E), and 6) divided nerve+Wet PEDOT–SIS (FIG. 18F);

FIG. 19 depicts fluffy PEDOT connections polymerized on decellular nerve (DN) by using an electro-chemical method;

FIG. 20 depicts an ex vivo impedance measured at 10 Hz, 100 Hz, and 1000 Hz for a Dry and Wet PEDOT coated decellular nerve;

FIG. 21 depicts an ex vivo surface charge density (C/mm$^2$) for the Dry and Wet PEDOT coated decellular nerve;

FIG. 22 depicts the successful reinnervation of transferred skeletal muscle neurotized by the residual stump of a peripheral nerve. Neuromuscular junctions (NMJ) indicate successful reinnervation of the muscle;

FIG. 23 depicts experimental groups with the Rat Peroneal Nerve. Sham: nerve exposed but left intact. Primary Repair: nerve divided, then immediately repaired. Divided Nerve: nerve divided, and distal segment excised. SIS: nerve divided and coapted to a scaffolding of SIS; distal segment excised. Dry PEDOT+SIS: nerve divided and coapted to a scaffolding of SIS coated with Dry PEDOT; distal segment excised. Wet PEDOT+SIS: nerve divided and coapted to a scaffolding of SIS coated with Wet PEDOT; distal segment excised;

FIG. 24 depicts a schematic of the peripheral nerve interface. The peroneal nerve is divided, then coapted to a scaffold that has been polymerized with a conductive polymer;

FIG. 25 depicts a comparison of Behavioral, Raw Histomorphometric, and Derived Histomorphometric Data. Data are represented as Z-scores. $Z=(x-\mu)/\sigma$, where x is the mean of a given experimental group, μ is the mean of all animals in the study, and σ is the standard deviation of all animals in the study;

FIGS. 26A-26F depicts histology of Rat Peroneal Nerve Samples. Sham shows large nerve fibers with thick myelin sheaths (FIG. 26A), Primary Repair has smaller fibers and less myelin (FIG. 26B), Divided Nerve (FIG. 26C), SIS (FIG. 26D), Dry PEDOT+SIS (FIG. 26E), Wet PEDOT+SIS (FIG. 26F). Toluidine-blue stained samples imaged at 1000×;

FIG. 27A-27F illustrates nerve histology of test groups, sham (FIG. 27A), autograft (FIG. 27B), decellular nerve (FIG. 27C), DryPEDOT (FIG. 27D), WetPEDOT (FIG. 27E), and no graft (FIG. 27F);

FIG. 28 depicts fluffy PEDOT connections polymerized on decellular nerve (DN) by using an electro-chemical method;

FIG. 29 depicts a plot of impedance measured by Electrical Impedance Spectroscopy. *Indicates significantly different from dehydrated decellular nerve, $\alpha <= 0.05$; and FIG. 30 depicts a plot of specific charge density measured by Cyclic Voltammetry. * Indicates significantly different from dehydrated decellular nerve, $\alpha <= 0.05$.

It should be noted that the figures set forth herein are intended to exemplify the general characteristics of materials, devices, and methods among those of the present technology, for the purpose of the description of certain embodiments. These figures may not precisely reflect the characteristics of any given embodiment, and are not necessarily intended to fully define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The regenerative peripheral nerve interface (RPNI) of the present disclosure addresses shortcomings of other technologies. For example, current generations of cuff electrodes do not intimately integrate with the neural tissue nor do they provide biologically active targets that prevent the continued formation of neuromas. Targeted muscle reinnervation provides a biological target and means for signal amplification, but has very limited resolution preventing high fidelity motor and sensory function. By incorporating living muscle in the RPNI, a microscale targeted muscle reinnervation (TMR) system is created that can be placed on single nerve endings. By using conducting polymer coated protein scaffolds, the net surface area of an electrode is increased by reducing the local charge density and improving signal transport. A mechanical gradient from stiff to soft keeps soft, delicate biological structures away from the rigid engineered devices that are involved in signal transduction. An increased flexibility reduces biofouling due to micromotion of the electrode, electrode tether breakage, and poor signal to noise ratio.

An important aspect of the RPNI is that it provides the ability to use living biological tissues as signal transducers, while preventing the formation of neuromas which not only cause clinical pain but are the source of substantial signal interference. Additional biotic and abiotic materials can be added for containment (SIS), signal preservation (conductive polymer), and signal relay (electrode).

A challenge associated with interfacing engineered devices with living systems is the need to accommodate the dramatic differences in mechanical, electrical, ionic, and biological properties between these components. Engineered devices have typically been made of rigid, solid components, and these are extremely stiff. Electrical conductivity is typically accommodated by inorganic metals or semiconductors. Biological tissues on the other hand are organic, living, laden with water, and ionically conductive.

In various aspects, the present disclosure provides a regenerative peripheral nerve interface (RPNI) for a subject comprising: an insulating substrate, at least one metallic electrode deposited onto the insulating substrate, a portion of the electrode surface having a layer of a first conductive polymer and a layer of decellularized small intestinal submucosa (SIS) coating a portion of the electrode, wherein a second conductive polymer is electrochemically polymerized through the SIS to form an electrically and ionically conductive structure. In other aspects, the RPNI further comprises a layer of muscle tissue contacting the SIS. In yet other aspects, the RPNI is wrapped around the end of a severed peripheral nerve in the subject.

In various aspects, the present disclosure provides a regenerative peripheral nerve interface (RPNI) for a subject comprising an insulating substrate, at least one metallic electrode disposed on or formed in the insulating substrate. The insulating substrate and the at least one metallic electrode thus form a thin-film array. A portion of an exposed surface of the at least one metallic electrode has a layer of a first conductive polymer. A portion of the exposed surface of the at least one metallic electrode also can have a layer of biotic or abiotic tissue as a coating, such as decellularized small intestinal submucosa (SIS) coating. A second conductive polymer is electrochemically polymerized through the SIS to form the regenerative peripheral nerve interface.

In certain variations, at least one metallic electrode can be disposed on the insulating substrate or can be deposited thereon. In other variations, the insulating substrate may be applied over an underlying metallic material (masked in certain regions to form an exposed surface of the one or more metallic electrodes). In various aspects, such a regenerative peripheral nerve interface is capable of interfacing with tissue in a subject. In certain aspects, the regenerative peripheral nerve interface is encapsulated with a layer of muscle tissue in contact with the SIS coating. Thus, the regenerative peripheral interface is capable of being implanted on at least one nerve ending of the peripheral nerve of the subject. In other aspects, the regenerative peripheral interface is capable of connecting with at least one sensor of a prosthetic device. For example, in certain variations, the regenerative peripheral nerve interface is connected to at least one sensor of a prosthetic device in a subject, and the regenerative peripheral nerve interface is capable of controlling the prosthetic device.

The present technology includes methods for reliable, long-term interfacing of peripheral nerves with metallic and semiconducting electrodes using a hybrid device termed a regenerative peripheral nerve interface (RPNI). In various aspects, the RPNI provides a method for the stable integration of stiff, inorganic, inert engineered devices into soft, living, wet organic tissue. The RPNI system involves several layers including an insulating substrate, electrodes, and conducting polymers deposited onto porous protein scaffolds, free muscle grafts, and then finally the motor and sensory peripheral nerves. Referring to FIGS. 1A-1C, the RPNI 10 comprises an insulating substrate 12, electrodes 14a, 14b, and conducting polymers 16, 18 deposited onto porous protein scaffolds 20, free muscle grafts 22, and then finally the motor and sensory peripheral nerves 24. FIGS. 1A-1C illustrate a hybrid, multi-layered interface that can interface between rigid metallic and semiconductor electrodes (needed for interfacing with rigid, electronically conducting engineered prosthetics) and soft, ionically conductive neural tissue. The present technology provides a RPNI that is a multi-layered, microscopic device that creates an environment where the neurons can regenerate, reinnervate and create stable, biologically active connections with muscle or sensory cells. In various aspects, the thin-film array has a length of less than or equal to about 1.5 mm, and a thickness of less than or equal to 50 μm.

The present disclosure provides that the RPNI based on the present technology incorporates both biotic and abiotic materials. U.S. Food and Drug Administration (FDA)-approved biologically derived tissues can be used in the motor and sensory RPNI. One biotic material is acellularized small intestinal submucosa (SIS) is a thin, sterile, nonimmunogenic porcine material. When hydrated and implanted, it is flexible, becomes vascularized, and incorporates into tissue surrounding the RPNI. SIS provides a semi-permeable container for the RPNI and stabilizes it. The distal end of select function fascicle(s) of the peripheral nerve are then sutured to skeletal muscle grafts which have been placed inside of the SIS container. A second piece of SIS is then electrochemically polymerized with an abiotic material, poly(3,4-ethylenedioxythiophene) (PEDOT), PEDOT is known to decrease impedance and increase electrical conductivity and capacity. A multiarray, planar, micro-polyimide electrode is embedded in the PEDOT coated SIS. The SIS is a biologically derived, soft, pliable, commercially available, and commonly used for clinical applications in humans. In addition, PEDOT can be easily polymerized on the surface of SIS and the electrode can be sewn to it.

The present disclosure provides that the RPNI uses an insulating substrate. In various aspects, the insulating substrate is selected from the group consisting of: poly-paraxylylene (parylene), polyimide, silicon dioxide and combinations thereof. In various aspects, the present disclosure provides that at least one metallic electrode is deposited on the insulating substrate. As illustrated in FIGS. 1A-1C, interconnects 14a of the electrodes 14b are insulated except at the surfaces of the electrodes themselves. In various aspects, the at least one metallic electrode is composed of a metallic material. Herein the term "metallic material" refers to a material that is not a metal within the normal definition, but which has the metal-like properties that are desired in certain appropriate applications. The metallic material is selected from a group consisting of Gold (Au), Platinum (Pt), Iridium (Ir), Palladium (Pd), Tungsten (W), Stainless Steel (SS), Indium-Tin-Oxide (ITO), Zinc, Titanium (Ti) and their alloys and oxides and combinations thereof.

Figure 2:
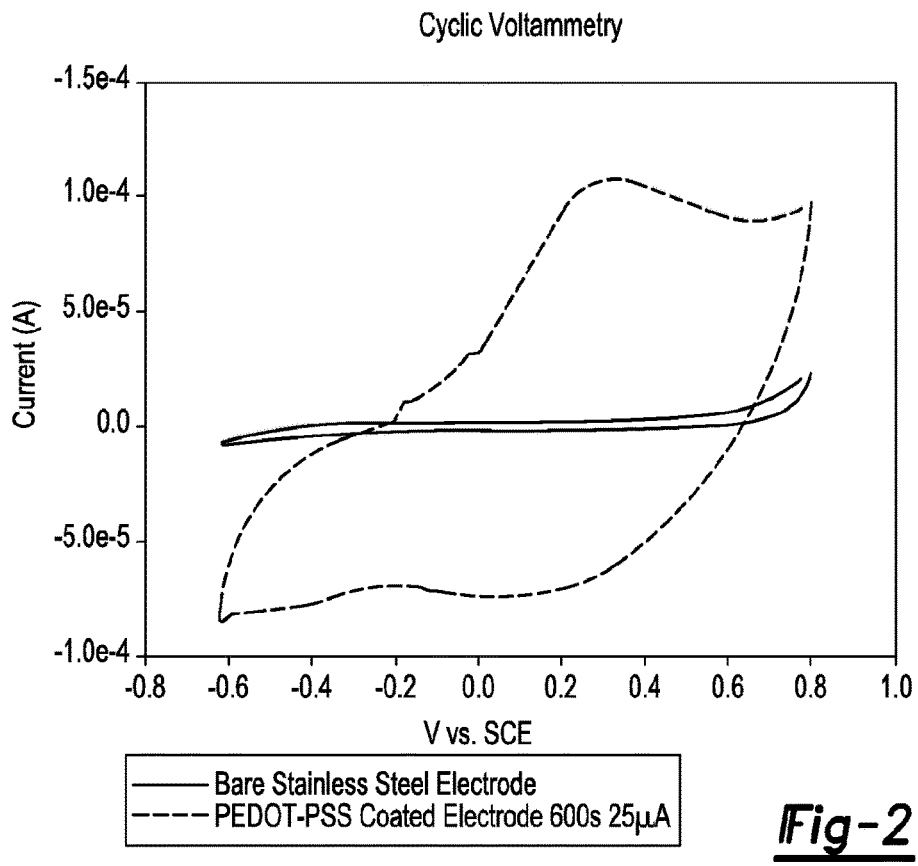
FIG. 2 depicts cyclic voltammetry data for electrodes coated with poly(3,4-ethylenedioxythiophene)(PEDOT) polymer compared to uncoated stainless steel electrodes.
Figure 3:
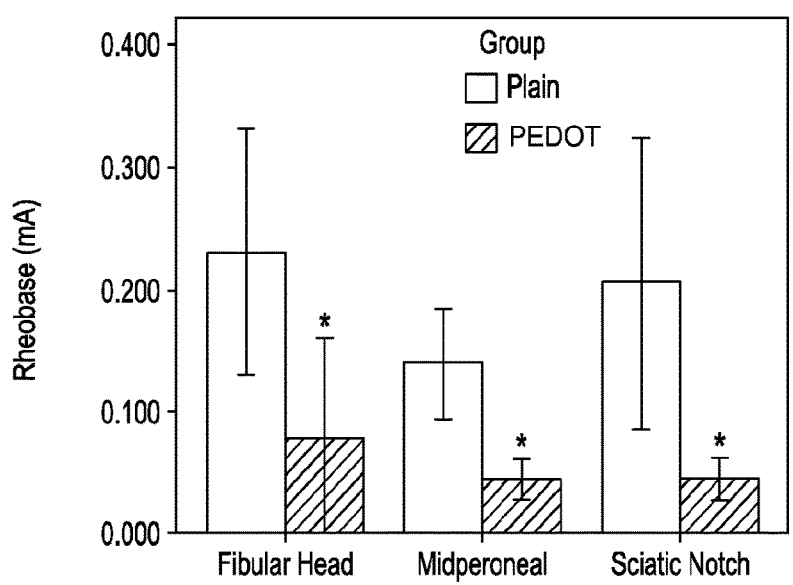
FIG. 3 depicts a rheobase measurement with a poly(3,4-ethylenedioxythiophene)(PEDOT) coated electrode compared to a plain electrode.

In other aspects, the at least one metallic electrode comprises a non-metallic material. The non-metallic material is selected from a group consisting of: poly(3,4-ethylenedioxythiophene) (PEDOT), poly(pyrrole), polyaniline, polyacetylene, polythiophene, natural or synthetic melanin, their derivatives and combinations thereof. In various aspects, poly(3,4-ethylenedioxythiophene) (PEDOT) is the non-metallic material. Referring to FIG. 2, needle electrodes coated with PEDOT electroconductive polymer gave a lower impedance and higher charge density than uncoated stainless steel electrodes. PEDOT coated electrodes have more robust cyclic voltammetry than stainless steel electrodes; this allows for a greater range of applied current. Additionally as illustrated in FIG. 3, PEDOT electrodes also have significantly a decreased rheobase. PEDOT coated electrodes are more sensitive and have a higher fidelity than uncoated electrodes. BT-DOT (Biotectix, Ann Arbor, Mich.) may also be used as the non-metallic material.

In various aspects, at least one metallic electrode is deposited onto the insulating substrate forming a thin-film array. Based on the present disclosure, the thin-film array comprises from 1 to 32 electrodes, has a diameter of less than or equal to about 1.5 mm, a length of less than or equal to about 3.6 mm, and a width of less than or equal to about 3.6 mm, and a thickness of less than or equal to 15 μm. In various aspects, the thin film arrays may be formed in two platform designs: epineurial and epimysial. In a non-limiting example, the arrays may be 15 μm thick with 32 regularly spaced electrode sites. Electrodes have an integrated interconnect that terminates in a tab with 32 bond pads that connect to individual electrode sites. A percutaneous connector is mounted on a custom printed-circuit board, which is then wire bonded to the bond pads. The dimensions of arrays in open configuration may be 5 mm×1 mm for epineurial and 2 cm×1 cm for epimysial electrode platforms.

Figure 4:
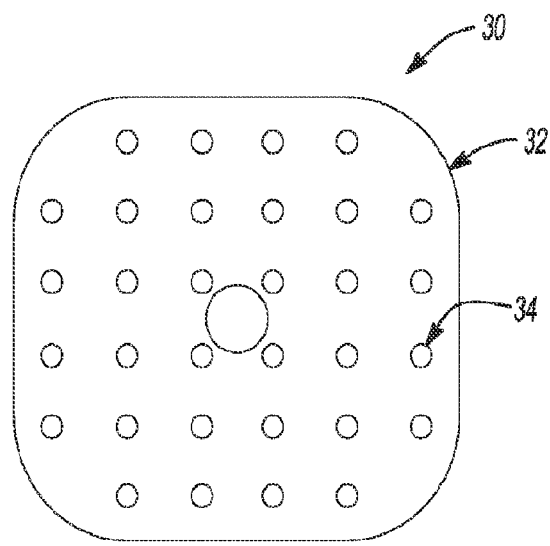
FIG. 4 illustrates a non-limiting example of an epimysial electrode thin-film array.

In a non-limiting example, referring to FIG. 4, the thin-film polyimide arrays 30 have been designed as an epimysial platform 32 for incorporation in the RPNI as an electrical and mechanical bridge between the soft peripheral nerve and the hard "wire." The dimensions of the open configuration multiarrays can be about 10×20 mm in size, from about 15 to about 38 μm in thickness, and can have 32 evenly spaced electrode sites 34 for stimulation and recording. These dimensions are merely exemplary for certain preferred variations; however, other dimensions are contemplated. In various aspects, the electrodes comprise an integrated interconnect that terminates in a tab with 32 bond pads that connect to individual electrode sites. A percutaneous connector may be mounted on a custom printed-circuit board, which can then be wire bonded to the bond pads. Additionally, suture holes allow for surgical adhesion increase stabilization and prevent straining of the array.

In various aspects, a portion of the at least one metallic electrode surface having a layer of a first conductive polymer. The first conductive polymer selected from a group consisting of: poly(3,4-ethylenedioxythiophene) (PEDOT), poly(pyrrole), polyaniline, polyacetylene, polythiophene, natural or synthetic melanin, their derivatives and combinations thereof. BT-DOT (Biotectix, Ann Arbor, Mich.) may also be used as the non-metallic material. A portion of electrode sites can have a conductive polymer known as BT-DOT (Biotectix, Ann Arbor, Mich.). When BT-DOT is applied to the recording and stimulating electrodes it significantly reduces the amount of current needed to evoke a muscle tissue response. In various aspects, the first conductive polymer comprises poly(3,4-ethylenedioxythiophene) (PEDOT). PEDOT allows nerve signals from the biotic nerve tissue to cross a 20 mm graft of acellular tissue polymerized with PEDOT and continue to propagate through the distal end of the grafted nerve.

The present technology provides that muscle cells embedded on a soft, biologically active protein scaffold derived from acellular tissue such as small intestinal submucosa, SIS (Cook Inc™). In certain aspects, the electrodes are coated with a layer of decellularized small intestinal submucosa (SIS) a porous protein matrix that consists primarily of collagen but that also has natural extracellular matrix adhesion proteins such fibronectin and laminin. SIS is a resorbable bioscaffold that has been extensively used in reconstructive surgeries including arterial grafts, bladder repair, and wounds. SIS promotes interactions with cells through integrin peptide sequences such as those found in fibronectin.

Figure 5A:
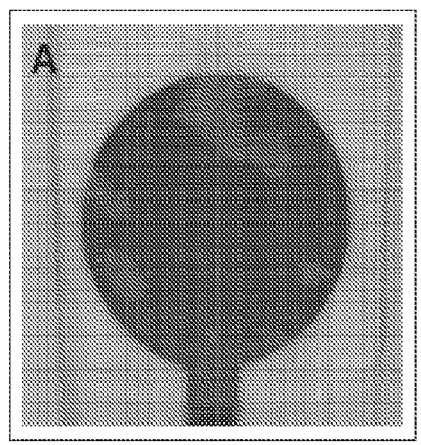
FIGS. 5A-5B illustrate a top view (FIG. 5A) and cross-section view of poly(3,4-ethylenedioxythiophene)(PEDOT) electrochemical polymerized through a layer of decellularized small intestine submucosa deposited on an electrode (FIG. 5B) in accordance with the present disclosure.
Figure 5B:
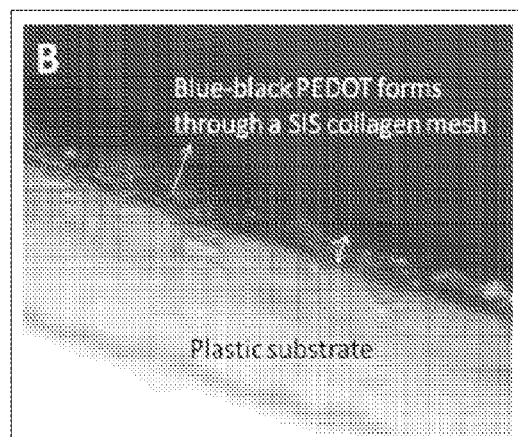

In various aspects, a second conductive polymer is electrochemically polymerized through the SIS to form the RPNI. Referring to FIGS. 5A-5B, illustrates the RPNI plus an electrode with the second conductive polymer such as PEDOT electropolymerized through the SIS. This configuration as multiple fine wire conductor provides solutions that enhance electrode sensitivity and reduce biofouling with time. In various aspects, the second conductive polymer is selected from the group consisting of: poly(pyrrole), polyaniline, polyacetylene, polythiophene, ester derivative 3,4-propylenedioxythiophene (ProDOT), natural or synthetic melanin their derivatives and combinations thereof. The SIS scaffold is itself coated with a second conductive polymer that is electronically and ionically active such as poly(3,4-ethylenedioxythiophene) (PEDOT). The second conductive polymer facilitates charge exchange between the ionic electrolyte (in the tissue) and the hole and electron transport of the metal and semiconductor substrate. The second conductive polymer on the SIS is interfaced to a locally deposited first conductive polymer electrochemically grown on the surface of metallic electrode. In various aspects, second conductive polymer (such as PEDOT) is then electrochemically grown up and through the SIS, creating an electrically and ionically conductive open structure that can surround and communicate with the living muscle and peripheral nerve fibers. In a non-limiting example, the second abiotic conductive polymer such as poly(3,4-ethylenedioxythiophene) (PEDOT) allows nerve signals from the biotic nerve tissue to cross a 20 mm graft of acellular tissue polymerized with PEDOT and continue to propagate through the distal end of the grafted nerve. The second conductive polymer allows the supporting scaffold (SIS) to remain compliant, thus preventing high sheer stresses in regions where soft, pliable nervous tissue contacts hard, rigid, inorganic materials. Other polymers and electrochemical polymerization techniques can be used that allow for low impedance conductive polymer microflowers which functionally bridge from the microfabricated electrode through the SIS scaffolds.

In certain aspects, a layer of muscle tissue is laid on the device. The layer of muscle, in various aspects is an autologous muscle graft. The muscle grafts are able to integrate into the porous conductive polymer-coated SIS and provide a stable, soft interface that is highly reliable, intimate, and mechanically compliant. In certain aspects, the RPNI comprises a branch or fascicle of residual peripheral nerve stump and small sections of freely grafted skeletal muscle. The skeletal muscle graft is harvested from a non-essential muscle in the residual limb. The muscle graft is from about 1.5 cm to about 5 cm long and from about 1 cm to about 2 cm in diameter.

In other aspects, the present disclosure provides a method of forming a regenerative peripheral nerve interface, the method comprising forming a regenerative peripheral nerve interface by coating a portion of at least one metallic electrode with an insulating substrate, wherein the insulating substrate defines a thin-film array, depositing a first layer of a conductive polymer onto the portion of the at least one metallic electrode; and coating at least a portion of the at least one metallic electrode with a layer of decellularized submucosa, wherein a second conductive polymer is electrochemically polymerized through the submucosa to form the regenerative peripheral nerve interface.

In a non-limiting example, tendon-like areas at the end of each harvested skeletal muscle are sutured to underlying fascia or bone in the area of the amputation. The skeletal muscle graft is splayed open along the length of the muscle fibers and the stump of the residual peripheral nerve is sutured inside the muscle to allow muscle reinnervation through the neurotization process. No attempt is made to vascularize the graft as these small constructs are quickly revascularized by collateral blood flow. The graft and nerve are then encapsulated by a very thin layer of acellular, nonimmunogenic small intestine submucosa (SIS). These devices are coupled to a thin microfabricated electrode (e.g., with 32 contacts), protein tissue scaffolds, physiological fibrin glue, and bioactive conducting polymer (CP). The RPNI bridges the severed sensory and motor nerve endings to skeletal muscle. This abiotic-biotic interface mediates the differences in physical properties between the inorganic, stiff, electrically-conducting metal contacts and the living, delicate, wet, ionically-conducting neural cells.

Figure 6:
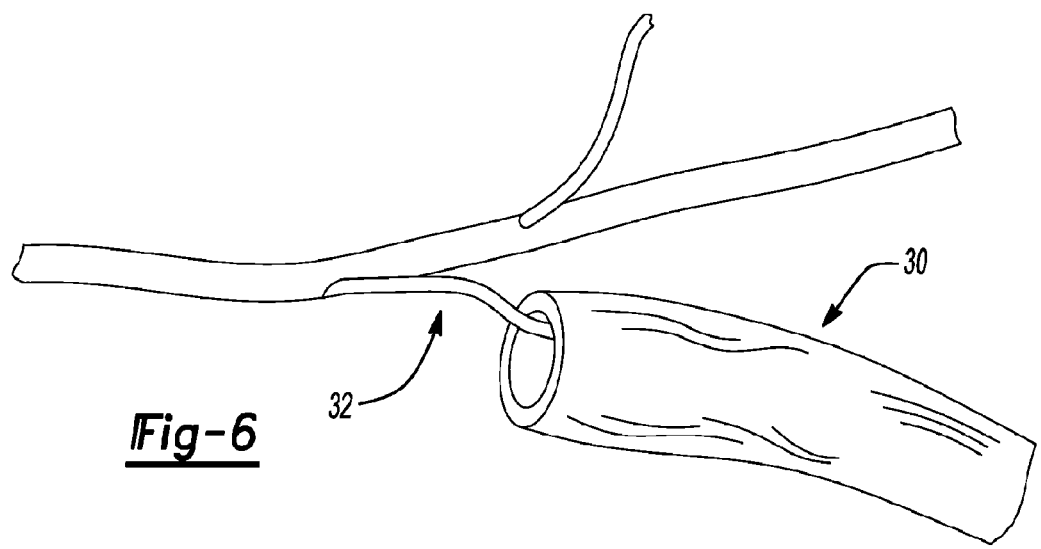
FIG. 6 illustrates a muscle graft and a severed nerve encapsulated by a layer of acellular, nonimmunogenic small intestine submucosa (SIS) and wrapped around the end of the severed nerve in accordance with certain aspects of the present disclosure.

In certain aspects, the devices are wrapped around the end of a severed peripheral nerve. Referring to FIG. 6, the muscle graft and the severed nerve are then encapsulated by a layer of acellular, nonimmunogenic small intestine submucosa (SIS) 30 and wrapped around the end of a severed nerve 32. The nerves regenerate into the RPNI and reinnervate the muscle, creating stable neuromuscular junctions with the muscle grafts. This muscle reinnervation prevents the long term development of neuromas, which can be the source of pain and signal interference. Because of the layered structure of the RPNI, the stiff metal electrodes are kept away from the nerves, preventing problems with local stresses and strains that arise when soft tissue is in direct contact with engineered devices. The materials also accommodate the inevitable need to transduce charge from electron-dominated (in the metal wire) to ion-dominated (in the living tissue).

In various aspects, the regenerative peripheral nerve interface is implanted on at least one nerve stump of a peripheral nerve of the subject. The surgery implantation is a safe operation which avoids opening body compartments. In other aspects, the regenerative peripheral nerve interface is connected to at least one sensor configured to control a prosthetic device. The present disclosure provides RPNI technology that allows nerve fibers which previously directed movement in the thumb of an intact arm to continue to direct movements for the thumb of the prosthesis. The sensors on a prosthetic thumb will connect with the RPNI containing sensory nerve fibers which prior to amputation extended to the thumb. Controlling a prosthetic will be rapid and less fatiguing as it will be very intuitive. In these instances, there is no need for re-learning since all motor and sensory nerves will continue to perform the functions they always performed, even prior to limb loss. A sensory connection between electronics and the peripheral nervous system is established—artificial pressure sensors and mathematical algorithms are used to modulate electronic signals at RPNIs to elicit action potentials (APs). Energy sourced to the nerve is also reduced. A signal modulation algorithm that elicits the sensation of light touch over a range of unique, discriminable pressures is also provided.

The RPNI involves focused and coordinated aspects of tissue engineering, neural interface development, materials science development, and systems engineering. These include development of a stable, reliable, and high fidelity electrical connectivity between motor and sensory fascicles and electronics for control of a downstream prosthetic device. Tissue engineering is combined with neural interface technologies and materials science to create the regenerative peripheral nerve interface. These further include supporting downstream electronics and circuitry as well as the decoding algorithms for efferent motor signals and encoding algorithms for sensory stimulation. The present disclosure provides a closed-loop neural control of a prosthetic device with multiple channels, durability of that interface by placing the system under substantial mechanical, electrical, and biologic stress, and shows persistent high fidelity function motor and sensory function.

Figure 7:
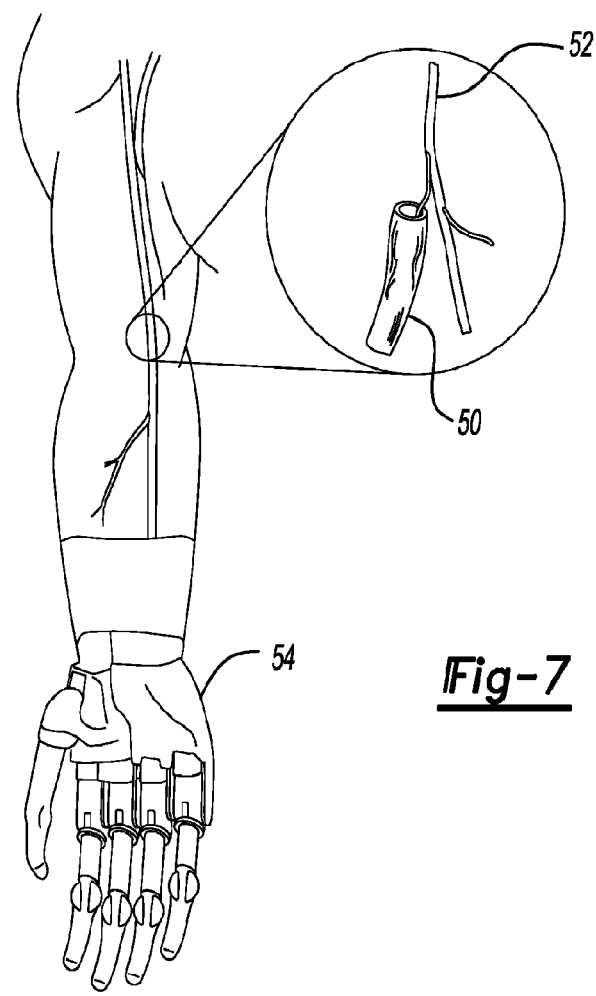
FIG. 7 illustrates the regenerative peripheral nerve interface and a prosthetic device in accordance with certain aspects of the present disclosure.

The present technology applies advances in biology, surgery, materials science, modeling, and electronic systems to form a fully integrated, bidirectional RPNI that is amenable to clinical translation. In yet other aspects, the present disclosure provides an interfacing device for interfacing between a peripheral nerve of a subject and prosthetic device, the interfacing device comprising: an insulating substrate, at least one metallic electrode deposited onto or integrated into the insulating substrate defining a thin-film array, a portion of the electrode surface having a layer of a first conductive polymer, a layer of decellularized small intestinal submucosa (SIS) coating a portion of the electrode, wherein a second conductive polymer is electrochemically polymerized through the SIS to form a regenerative peripheral nerve interface and a layer of muscle tissue contacting the regenerative peripheral nerve interface. In some aspects, a permanent implantable peripheral nerve interface device provides high-fidelity motor control and sensory feedback of an advanced prosthetic arm and hand for upper-extremity amputees. An innovative tissue engineered matrix is used to form a permanent structural and electrical interface with regenerating axons from an individual fascicle of severed peripheral nerve. Referring to FIG. 7, illustrates the RPNI with the conductive polymer coated SIS scaffold 50 implanted around a severed peripheral nerve stump 52 and the RPNI is located in close proximity to a prosthetic device 54.

Within mainly motor-related fascicles, this biosynthetic matrix provides the means to obtain graded multi-dimensional control signals by recording from small or large populations of efferent axons. Likewise, within mainly sensory fascicles, the matrix provides the means for graded multichannel sensory input by selectively stimulating small or large populations of afferent fibers. For mixed-function fascicles, the matrix interface provides the ability for both recording motor signals and stimulating sensory feedback signals. The peripheral nerve interface device comprises multiple fascicle matrix interfaces (motor and/or sensory) that are each connected to an implantable miniaturized wireless electronics interface for communication to an external controller.

The RPNI includes skeletal muscle, which has been grafted from the amputee, and a conductive polymer grown through living protein scaffolds such SIS. The conductive polymer electrically and mechanically bridges the gap between the soft, pliable divided peripheral nerve and the inorganic downstream electronics. Residual peripheral nerve branches are sutured into the grafted muscle and sprouts emerge from the peripheral nerve stump and reinnervate the grafted muscle fibers. The pain which is produced by cut nerve endings and neuromas is avoided because permanent connections are formed in the muscle. Multiple RPNIs can be fit to peripheral nerve branches or fascicles to perform efferent (motor) action potential recordings or afferent (sensory) action potential stimulation.

The second conductive polymer filaments can be in contact with RPNI nerve fibers, muscle fibers, and electrodes. The second conductive polymer coating on the SIS protein can be less than fully conformal; access can be retained to the tissue's native integrin binding sites which remain after the decellularization process is completed. The option of locally sampling tissues within the construct can also be preserved. Additional innovations include advantageous placement of the RPNI. Locating the RPNI close to the prosthetic allows: for access to peripheral nerves after they have sorted themselves into location specific motor and sensory functions; for less interference from surrounding neural tissue, for less cross talk between RPNI; for shorter access length to the prosthetic; for more degrees of freedom, faster intuitive learning, and neuroma-free recovery. Based on the present disclosure, the design of devices for human use and haptic display allow for rapid prototyping and fabrication techniques. These include laser cutting, fused deposition modeling (FDM), CNC, water-jet cutting, polydimethylsiloxane (PDMS) molding and bonding, and shape deposition manufacturing (SDM).

In conjunction, the RPNI, the bioactive conductive polymer, and a polyimide electrode provide for closed loop neural control of a prosthetic. In a non-limiting example, the use of the epimysial electrode further benefits the development of a prosthetic ankle joint. Two methods are available to decode the RPNI signal amplitude and waveform for the joint moment to be imposed by a motor on the corresponding prosthetic joint or joints. The first is based on a characterization of the response of the RPNI signal to proximal stimulation of its nerve bundle. Since the response of intact muscle to proximal nerve stimulation (in terms of muscle force and length and/or joint moment and angle) is already well known in the art, the response of a RPNI-driven motorized prosthetic joint can be tuned to mimic the action of intact muscle. The second method is simply ad-hoc tuning. Ad-hoc tuning has proven quite sufficient for mapping electromyographic (EMG) signals onto joint motor actions, as evidenced by the success of myoelectric control in upper-limb prostheses. Ad-hoc tuning of EMG signals are also effective for use in generating assist and amplification of motor intent. Likewise, the success of simple tuning procedures in targeted nerve reinnervation attests to the relative simplicity of using EMG as a basis for control, even when drawn from muscles that have undergone denervation and subsequent reinnervation with alternative nerve fibers.

In various aspects, the RPNI is implanted on at least one nerve stump of the peripheral nerve of the subject. In an non-limiting example, the RPNI may be surgically constructed and implanted within the residual limb of an amputee and comprises living skeletal muscle grafts which are surgically attached to the ends of severed motor and sensory fascicles of the nerves that formerly innervated the limb, such as the arm and hand. In various aspects, the layer of muscle tissue is autologous to the subject. The isolated autogenous muscle transplants are naturally reinnervated through robust neural sprouting and elongation processes. A layer of soft electroconductive polymer can be polymerized on the surface of an acellular, nonimmunogenic, semipermeable, commercially available, intestinal scaffold. The polymer can serve as an interface to electrically and mechanically bridge the soft, pliable neuromuscular unit with a polyimide multiarray stimulating and recording probe. A layer of the scaffold material can be wrapped around the entire RPNI to provide support and electrically insulate the RPNI from surrounding tissues.

The present technology demonstrates the biological stability of a motor and sensory RPNI, the durability of the RPNI with an implanted electrode, and the reliability of the electronic interfaces to the RPNI. In various aspects, the RPNI is connected to at least one sensor configured to control the prosthetic device. As illustrated in FIG. 8, the brain sends signals through a motor RPNI to motor components in the prosthesis. Feedback signals return from sensors in the prosthesis through a sensory RPNI back to the central nervous system. The present technology may provide stable, long-lasting and high fidelity neural control and sensory feedback that can be interfaced to high fidelity prosthetic limbs for use in humans. In various aspects, the implanted regenerative peripheral interface is biologically stable for about a year to the lifetime of the subject.

The RPNI involves focused and coordinated aspects of tissue engineering, neural interface development, materials science development, and systems engineering. These include development of a stable, reliable, and high fidelity electrical connectivity between motor and sensory fascicles and electronics for control of a downstream prosthetic device. Tissue engineering is combined with neural interface technologies and materials science to create the regenerative peripheral nerve interface. These further include supporting downstream electronics and circuitry as well as the decoding algorithms for efferent motor signals and encoding algorithms for sensory stimulation. This allows for closed-loop neural control of a prosthetic device with multiple channels, durability of the interface under mechanical, electrical, and biologic stress, and high fidelity function motor and sensory function. The RPNI electronics can include analog system components and digital interfaces. This includes a processor controlled pulsing current source as well as the signal conditioning and the analog-to-digital conversion (ADC) and the digital-to-analog conversion (DAC) for the motor and sensory signals received from the nerves (RPNI-M) and transmitted to the nerves (RPNI-S), respectively.

The following specific examples are provided for illustrative purposes of how to make and use the compositions, devices, and methods of this technology and, unless explicitly stated otherwise, are not intended to be a representation that given embodiments of this technology have, or have not, been made or tested.

EXAMPLES

Example 1

Nerve Regeneration in the Presence of Conductive Polymers

In the following example, an amputee's residual peripheral nerves are interfaced with processors that receive and transmit signals for prostheses control. PEDOT (3,4-polyethylenedioxythiophene) is an anisotropic, conductive polymer that beneficially reduces tissue impedance. PEDOT can be polymerized into nonconductive, processed decellular nerve (DN) leaving it highly conductive but stiff (DryPEDOT), or, less conductive but pliable (WetPEDOT). The nerve regeneration was tested in a rat peripheral nerve interface (PNI) environment and PEDOT biocompatibility was also evaluated.

A 15 mm, peroneal nerve gap was reconstructed with one of five nerve derived materials: Sham, Autograft, DN, DryPEDOT, and WetPEDOT, or not reconstructed: Gap, (n=8/group). A single layer of acellular submucosa surrounded each graft as in peripheral nerve interfaces. After 90 days, evaluations were completed for muscle force, nerve conduction, and midgraft morphology.

The results report for gap reconstruction groups, as no nerves bridged the gap in the Gap group. As illustrated in FIGS. 9A-9F, nerve fibers successfully regenerated in each group as confirmed by evoked compound muscle action potential presence. Conduction velocity was fastest for DryPEDOT and slowest for WetPEDOT groups. Muscle force was also recovered in each group. Nerve morphology rankings from normal to still reorganizing were: Sham>Autograft>DN>WetPEDOT>DryPEDOT. Both PEDOT groups had 75% less axon area than the DN. Electron micrographs of DryPEDOT show PEDOT greatly reduces DN conduit diameter.

TABLE 1

Modified Peripheral Nerve Grading System (Murji, A., et al., The role of intraoperative frozen section histology in obstetrical brachial plexus reconstruction. J. Reconstr. Microsurg., 2008. 24(3): p. 203-9.)

| Epineurium | Endoneurium | | | Perineurium | |
|---|---|---|---|---|---|
| Microfascicles | Free Space | Organization | Definition | Thickening | Microfascicles |
| None (1) | Normal (1) | Good (1) | Good (1) | None (1) | None (1) |
| Rare (2) | Mild increase (2) | Poor (2) | Poor (2) | Mild (2) | Rare (2) |
| Moderate (3) | Moderate (3) | None(3) | None (3) | Moderate (3) | Severe (3) |
| Severe (4) | Severe (4) | | | Severe (4) | |
| Extensive (5) | | | | | |

This scale is a modified version of what is described previously (Murji, Redett et al. 2008) Scores e.g. "None-1" indicates a score of 1 as no microfascicles were seen outside the epineurium. "Extensive-5" indicates a score of 5, which reflects barely recognizable epineurium/no epineurium, so microfascicles are observed throughout all section. "Rare-2", "Moderate-3", "Severe-3" are graded by density of microfascicles seen at epineurium. Nerves were evaluated independently by two observers.

TABLE 2

Statistical Summary of Quantitative Nerve Histology classified by Reconstruction type.

| | Surgical Groups | | | | | |
|---|---|---|---|---|---|---|
| | Sham | Autograft | Decellular Nerve | Dry PEDOT | Wet PEDOT | Gap |
| Number of Subjects | n = 8 | n = 8 | n = 8 | n = 8 | n = 8 | n = 8 |
| Axon Count | 877 ± 461 | 863 ± 297 | 552 ± 256 | 169 ± 240† | 190 ± 100† | 0 |
| Neural Area ($\mu m^2$) | 15168.2 ± 5639.3 | 9408.9 ± 5191.2 | 4442.3 ± 2809.9 | 998.2 ± 1380.3† | 1288.7 ± 815.4 | 0 |

TABLE 2-continued

Statistical Summary of Quantitative Nerve Histology classified by Reconstruction type.

| | Surgical Groups | | | | | |
|---|---|---|---|---|---|---|
| | Sham | Autograft | Decellular Nerve | Dry PEDOT | Wet PEDOT | Gap |
| Axon Density (1/μm²) | 0.019 ± 0.005 | 0.022 ± 0012 | 0.011 ± 0.008 | 0.003 ± 0.004*† | 0.004 ± 0.002 | 0 |
| Percent of Neural Area (%) | 3.48 ± 1.0 | 2.13 ± 0.75 | 9.03 ± 0.63 | 1.68 ± 0.24*† | 2.73 ± 0.18*† | 0 |
| Nerve histology grade | 6 ± 0 | 9.2 ± 1.9* | 12.8 ± 2.6*† | 20.5 ± 1.4*†‡ | pending | 22.0 ± 0*†‡ |

Values listed are mean ± SD, $p < 0.05$,
*indicates difference vs. Sham,
†indicates difference vs. Autograft,
‡indicates difference vs. Decellular Nerve.

TABLE 3

Statistical Summary of Muscle Force, Motor Action Potential Velocity and Nerve Histology Grade classified by Reconstruction type.

| | Surgical Groups | | | | | |
|---|---|---|---|---|---|---|
| | Sham | Autograft | Decellular Nerve | Dry PEDOT | Wet PEDOT | Gap |
| Number of Subjects | n = 8 | n = 8 | n = 8 | n = 8 | n = 8 | n = 8 |
| Maximum isometric tetanic force (mN) | 3119.3 ± 570.7 | 1591.7 ± 520.2* | 783.1 ± 685.6* | 232.2 ± 210.9*† | 82.1 ± 60.2*† | 0 |
| Action potential velocity (m/s) | 13.41 ± 2.68 | 13.85 ± 3.77 | 9.31 ± 1.46*† | 19.75 ± 2.85*†‡ | 5.73 ± 0.91*†§ | 0 |

Values listed are mean ± SD, $p < 0.05$,
*indicates difference vs. Sham,
†indicates difference vs. Autograft,
‡indicates difference vs. Decellular nerve,
§indicates difference vs. dry PEDOT Normal peripheral nerve regeneration occurs in a PNI environment. Peripheral nerve regeneration occurs in the presence of both Dry and Wet PEDOT. PEDOT may obstruct regeneration through DN conduits.

Example 2

Long Term Stability of Regenerative Peripheral Nerve Interfaces (RPNI).

Stability of Regenerative Peripheral Nerve Interfaces

An amputee's peripheral nerves with neuro-prosthetic arms possessing the latest robotic technology are interfaced. The regenerative peripheral nerve interface (RPNI) is constructed by implanting syngeneic muscle cells from one of two stages of muscle development, immature (myoblast) or mature (transferred muscle). A construct is formed from a decellular muscle with or without the conductive polymer poly(3,4-ethylenedioxythiophene), or PEDOT, which supports the muscle cells and allows implantation of the transected residual nerve within the RPNI. For all RPNI, spontaneous EMG, nerve conduction, and neuromuscular junction formation following in-situ maturation occurred. RPNI were sustained long term for both the myoblast and the muscle transfer groups.

Animal care and operative procedures were performed in accordance with the *United States Public Health Service Guide for the Care of Laboratory Animals* (National Institutes of Health, Public Health Service. *Guide for the Care of Laboratory Animals*. Bethesda, Md.: National Institutes of Health, Public Health Service, NIH Publication 86-23, 1985.) RPNI constructs (15×5 mm) containing the proximal end of the transected residual nerve and either myoblasts or transferred skeletal muscle were implanted in the rat thigh using a hind limb amputation model. Myoblasts were grown in culture for 14 days prior to RPNI implantation transferred muscle was donated by the same recipient rat. RPNI constructs were surrounded by plain decellular muscle (DM) or DM coated with the conductive PEDOT polymer. Normally innervated Control muscles were compared with four RPNI groups representing combinations of the independent variables: maturity stage and presence of conductive polymer. The experimental groups were: 1) myoblasts: a) (MyoCells, n=6), b) (MyoCells with PEDOT, n=3); 2) freely transferred muscle: c) (MusTran, n=9), and d) (MusTran with PEDOT, n=2). Three to 18 months following implantation, RPNI constructs were functionally assessed by measuring electrophysiologic recordings of spontaneous electromyography (EMG) and evoked nerve conduction (NCV). RPNI were processed histologically to identify muscle fibers and neuromuscular junction formation and individual muscle fiber cross sectional area (CSA) was measured.

At harvest, all RPNI constructs were covered by a thin capsule of scar tissue less than 1 mm in thickness. All RPNI constructs were well vascularized and without evidence of infection. When compared with Control muscle fibers, the MusTran RPNI fibers regenerated 33% of normal fiber CSA while MyoCell RPNI fibers matured to reach only 3% of Control fiber CSA. The measured peroneal nerve electrodiagnostics showed MusTran RPNI constructs performed comparably to Control muscle in compound muscle action potential (CMAP) latency, area, duration, and velocity as illustrated in Table 4 below. MyoCell RPNI recovered weaker function for CMAP amplitude and latency compared to MusTran RPNIs. Desmin labeling (Thermo Scientific #RB-9014, Fremont, Calif.) confirmed muscle cell phenotype in all groups as illustrate in FIGS. 10A-10D. Neuromuscular junction (NMJ) staining on MyoCell and MusTran RPNI muscle fibers showed extensive muscle fiber neurotization as illustrated in FIGS. 11A-11D.

Myoblasts and freely transferred muscle became functionally incorporated into RPNI constructs. Implantation of the transected proximal nerve endings led to RPNI innervation. Muscle and nerve tissues matured and their vital functions were sustained for up to 18 months in both myoblast and freely transferred muscle groups with or without scaffolds chemically polymerized with conductive PEDOT.

electrode array as a peripheral nerve interface-signal recording probe was tested. The feasibility of array in terms of biocompatibility, material integrity (electrical and mechanical) and surgical availability was also tested.

The thin-film electrodes are microfabricated polyimide thin-film arrays developed and provided by NeuroNexus Technologies, Inc. The design space of this technology provides a large variability in terms of electrode size, placement and packaging for chronic preparations. The arrays were flexible, planar, 15 microns thick with 32 regularly spaced electrode channels. In the surgical procedure, the rat peroneal nerve was exposed and divided. The thin-film polymer arrays were implanted around the proximal stump as a 'cuff' and secured with a small intestinal submucosa covering. Animals recovered for 6 weeks. At the 6 week end point, nerve specimens, including sections of the thin-film array, were explanted and primary results were obtained with histological evaluation. Additionally electrophysiology was performed to record preliminary results.

All animals recovered reasonable mobility. Gross examination of the thin-film array 6 weeks after implantation showed minimal gross tissue reaction. No major signs of inflammatory reaction, foreign tissue reaction were found. In histology the nerve morphology proximal to the remained organized. As show in FIG. 12, neither acute nor chronic inflammatory cells were observed histologically. Preliminary electrophysiology data suggested electrical stability of polyimide thin-film array after 6 weeks.

Based on these results a thin-film array is stable, biocompatible and surgically feasible material to be used for peripheral nerve interface.

TABLE 4

Comparisons for Control & Regenerative Peripheral Nerve Interface Groups.

| | | Groups | | |
|---|---|---|---|---|
| | Dependent Variable | Control | MyoCells | MusTran |
| Nerve Conduction to RPNI | Number in Each Group | 37 | 6 | 9 |
| | CMAP Amplitude, mV | 18.8 ± 8.1 | 0.4 ± 0.5* | 13.2 ± 11.0*,† |
| | CMAP Latency, ms | 1.4 ± 0.3 | 2.6 ± 2.7* | 1.5 ± 0.3† |
| | CMAP Area, mVms | 20.5 ± 9.8 | 0.9 ± 0.8* | 15.4 ± 12.6 |
| | CMAP Duration | 4.7 ± 6.1 | 2.3. ± 3.3 | 1.9 ± 0.2 |
| | Conduction velocity, M/s | 24.7 ± 4.6 | 14.5 ± 10.2* | 19.7 ± 6.8 |
| | Stimulation, mA | 2.8 ± 8.1 | 2.7 ± 8.1** | 17.1 ± 14.4* |
| | Stimulation duration, ms | 0.7 ± 0.8 | 0.4 ± 0.5 | 0.1 ± 0.0 |
| | Muscle Fiber CSA, mm$^2$ | 2151 ± 73 | 65 ± 95* | 704 ± 386*,† |
| Histology | | (n = 4) | (n = 2) | (n = 6) |

Compound Muscle Action Potential (CMAP);
Cross sectional area (CSA).
Significant results indicated by:
*less function than Control; † better than Myoblast Group,
**better than Muscle Transfer.
α ≤ 0.05.
mV = millivolt,
ms = millisecond,
M = meter;
mA = milliAmp.

Example 3

Peripheral Nerve Interface to Thin-Film Polyimide Electrode Arrays

In the following example, a peripheral nerve interface to provide motor signals to and record sensor feedback from prostheses is developed. In this study, a thin film polyimide Example 4

Soleus Grafts to Modulate Neuroma Formation in a Peripheral Nerve Interface

In the following example, a peripheral nerve interface (PNI) with motor and sensory capabilities for closed-loop neural control of an artificial limb is developed. The PNI uses the highly conductive polymer, poly(3,4-ethylenedioxythiophene) (PEDOT), to reduce impedance and limit biofouling. Problematic neuromas are disorganized nerve fibers that often accompany nerve lesions; they are painful and can be a source of signal interference. Muscle tissue is abundant and can be used as an end organ for regenerating nerves. The hypothesis is that embedding divided nerve into a free soleus graft will reduce neuroma formation for in a peripheral nerve interface.

In a rat model, the peroneal nerves are divided, and the proximal stump is coated to a scaffolding of small intestinal submucosa (SIS). PEDOT is electrochemically polymerized on these scaffolds. The contralateral soleus muscle is denervated, devascularized, and tenotomized. As illustrated in FIG. 13, it is then transferred to the ipsilateral operative field for peroneal nerve embedding. The study groups illustrated in FIG. 14 (n=8 per group) are as follows: Sham, Divided Nerve, SIS alone, SIS with Soleus, SIS with PEDOT, and SIS with PEDOT and Soleus. Tactile sensation is evaluated with von Frey filament stimulation at the operative site at 3 months and 6 months. Nerve cross sections are taken at 6 months. Morphometric analysis is performed at 1000× magnification and an unbiased sampling technique is used to quantify axon count and neural tissue in the neuroma.

On von Frey evaluation, lower sensitivity thresholds imply more pain due to neuroma formation within the PNI. Referring to FIG. 15, the Divided Nerve group was more sensitive than the Sham group at both 3 and 6 months. These findings validate von Frey testing as a measurement of pain, and by inference, neuroma formation. The PEDOT group had no statistical differences from the SIS group at 3 or 6 months.

At both the 3 and 6 month time points, PEDOT showed minimal differences in tactile sensitivity compared to SIS scaffolding alone. These data suggest that PEDOT alone has minimal effect on neuroma formation in the chronic phase. Final evaluations will include tactile sensitivity and histomorphometry of Soleus groups.

Example 5

Tactile Sensitivity after Soleus Grafting in a Peripheral Nerve Interface

In the following example, a regenerative peripheral nerve interface (RPNI) for neural control of an artificial limb is developed. The RPNI uses the conductive polymer, poly(3,4-ethylenedioxythiophene) (PEDOT), to reduce impedance and limit biofouling. Neuromas often accompany nerve lesions; they increase pain sensitivity and can cause signal interference. von Frey evaluations are used to evaluate sensitivity threshold. More sensitivity may imply more pain due to neuroma formation within the RPNI. Muscle can be used as an end organ for regenerating nerves. As a result a) tactile sensitivity is unaffected by the presence of PEDOT, and b) embedding divided nerves into free soleus grafts reduces tactile sensitivity.

In a rat model, the peroneal nerve is divided, and the proximal stump is coapted to a scaffolding of small intestinal submucosa (SIS). Animals designed to evaluate PEDOT are given scaffolds electrochemically polymerized with PEDOT. The contralateral soleus muscle is transferred to the ipsilateral thigh for peroneal nerve embedding. The study groups are as follows: Sham, SIS alone, SIS with Soleus, SIS with PEDOT, and SIS with PEDOT and Soleus. Tactile sensation is evaluated with von Frey filament stimulation at the operative site at 3 and 6 months. Statistical significance was determined by Kruskal-Wallis analysis.

Referring to FIG. 16, All of the experimental groups were more sensitive than the Sham group ($\alpha<0.06$), consistent with an intact nerve differing from a divided nerve. Adding Soleus, PEDOT, or a combination of the two to the SIS scaffolding did not result in measurable differences. Referring to FIG. 17, the presence of PEDOT and soleus muscle interact in their effect on sensitivity. The effect of PEDOT on sensitivity depends on the presence of soleus muscle. At 3 months of recovery, the addition of soleus appears to increase sensitivity, while at 6 months, the addition of soleus appears to decrease sensitivity.

PEDOT showed minimal differences in tactile sensitivity compared to SIS scaffolding alone. These data suggest that PEDOT alone has minimal effect on sensitivity (neuroma formation). The results also indicate that the effect of neurotizing soleus muscle has interactions with the effects of PEDOT as well as postoperative recovery time.

Example 6

Histologic and Tactile Evaluation of Chronic Neuromas from a Peripheral Nerve Interface In the following example, a peripheral nerve interface (PNI) with motor and sensory capabilities for closed-loop neural control of an artificial limb is developed. The PNI uses the highly conductive polymer, poly(3,4-ethylenedioxythiophene) (PEDOT), to reduce impedance and limit biofouling. Problematic neuromas are disorganized nerve fibers that often accompany nerve lesions; they are painful and can be a source of signal interference. The neuroma formation is unaffected by the presence of PEDOT at 3 and 6 months.

In a rat model, the peroneal nerve was divided, and the proximal stump was coapted to a scaffolding of small intestinal submucosa (SIS). PEDOT was polymerized on these scaffolds for two of the experimental groups. The first, Dry PEDOT, was chemically polymerized on the scaffold resulting in a stiff compound. The second, Wet PEDOT, was electrochemically polymerized on the scaffold resulting in a softer, more compliant compound. The study groups (n=8 per group) are as follows: Sham, Primary Repair, Divided Nerve, SIS alone, SIS with Dry PEDOT, and SIS with Wet PEDOT. Tactile sensation was evaluated with von Frey filament stimulation at the operative site at 3 months and 6 months. Nerve cross sections were taken at 6 months. Morphometric analysis was performed at 1000× magnification and an unbiased sampling technique was used to quantify axon count and neural tissue in the neuroma.

Referring to FIG. 18, on histologic evaluation, both SIS with Dry PEDOT and SIS with Wet PEDOT appear qualitatively healthier than divided nerve, but not significantly different than SIS alone. Table 5 below illustrates, the initial quantitative data from overall neural tissue reflects a similar finding.

TABLE 5

Histologic assessment of neuroma formation at 6 months.

| | Sham (n = 2) | Primary Repair (n = 2) | Divided Nerve (n = 2) | SIS (n = 2) | Dry PEDOT-SIS (n = 2) | Wet PEDOT-SIS (n = 2) |
|---|---|---|---|---|---|---|
| Axon Count | 283.5 ± 62.9 | 275.0 ± 134.4 | 315.0 ± 38.2 | 585.0 ± 103.2 | 539.0 ± 326.7 | 308.0 ± 137.2 |
| Neural Area ($\mu^2$) | 4523.9 ± 2655.6 | 2167.5 ± 329.2 | 2090.5 ± 1539.5 | 7169.8 ± 1094.6 | 4254.8 ± 1794.4 | 4000.8 ± 2431.7 |
| % Neural Tissue | 35.5 ± 11.8 | 23.7 ± 21.4 | 15.0 ± 1.9 | 29.5 ± 4.1 | 22.6 ± 13.1 | 18.9 ± 7.2 |

Data represented as mean ± 1SD.
Abbreviations:
SIS indicates Porcine small intestinal submucosa.
PEDOT indicates poly(3,4-ethylenedioxythiophene).

On von Frey evaluation, lower sensitivity thresholds imply more pain due to neuroma formation. Referring to Table 6 below, addition of Dry PEDOT to the SIS scaffold increased the sensitivity of the operative site when compared with the SIS scaffold alone at 3 months. However, neither Dry nor Wet PEDOT groups were significantly different from the SIS group at 6 months.

TABLE 6

Three and six month tactile sensitivity thresholds (g) to von Frey monofilament stimulation.

| | Sham (n = 8) | Primary Repair (n = 8) | Divided Nerve (n = 8) | SIS (n = 8) | Dry PEDOT + SIS (n = 8) | Wet PEDOT + SIS (n = 8) |
|---|---|---|---|---|---|---|
| 3 months | 0.63 g ± 0.76 g | 0.62 g ± 0.96 g | 0.10 g ± 0.15 g* | 0.22 g ± 0.33 g | 0.01 g ± 0.02 g*† | 0.32 g ± 0.32 g |
| 6 months | 1.03 g ± 1.08 g | 0.15 g ± 0.19 g | 0.07 g ± 0.10 g* | 0.20 g ± 0.30 g | 0.13 g ± 0.13 g | 0.15 g ± 0.15 g |

Values are the mean ± 1SD for the calculated 50% gram threshold.
Lower values reflect higher sensitivity.
*more sensitive than Sham, $p < 0.05$.
†more sensitive than SIS, $p < 0.06$.
Abbreviations:
SIS indicates Porcine small intestinal submucosa.
PEDOT indicates poly(3,4-ethylenedioxythiophene).

At the 6 month time point, both forms of PEDOT showed minimal differences in histologic changes and tactile sensitivity compared to SIS scaffolding alone. These data suggest that PEDOT has minimal effect on neuroma formation in the chronic phase and is a promising material for use in a peripheral nerve interface.

Example 7

Electromechanical Properties of Peripheral Nerve Interfaces

In the following example, a regenerative peripheral nerve interface for closed loop neural control of prostheses is developed. This interface integrates amputee's residual peripheral nerves with transferred skeletal muscle. The purpose of this study is a) to determine the nature of electrical and mechanical muscle properties 3 months after standard free muscle transfer with implantation of a residual nerve and b) to determine if successful neurotization takes place.

Rats (n=18) were divided into three groups: sham, standard free muscle transfer (Tran), and muscle transfer with residual nerve implantation (Tran+RN). During sham surgeries, the right leg was dissected to expose the soleus muscle and then sutured closed. For both Tran and Tran+RN groups the right soleus muscle was transferred between interstitial tissues of the left thigh, beneath the m. biceps femoris and parallel with the femur. In both Tran and Tran+RN groups the right tibial nerve was dissected free and divided. In the Tran+RN group the left peroneal nerve was divided and the proximal end sutured within the transferred muscle. After 90 days of implantation the transferred muscles were tested using both nerve conduction studies (NCS) and muscle force testing. For both NCS and muscle force testing, the peroneal nerve was stimulated at the sciatic notch. NCS testing measured stimulus threshold, amplitude, and number of active motor units. Muscle force testing measured maximal tetanic force generated. Specific force was calculated by dividing the tetanic force by the muscle cross sectional area.

As illustrated in Table 7 below, all transferred muscles survived throughout the entire study. Muscle mass for Sham was significantly higher than for Trans but not Trans+RN (Table 7). The stimulus threshold for Trans+RN was significantly lower than for Trans alone indicating increased muscle responsiveness to lower levels of current. The stimulus threshold for Trans+RN however was still higher than Sham. CMAP amplitude and duration for Sham were higher than both Trans and Trans+RN. Nerve implantation increased the tetanic force production of soleus muscle when compared to transferred muscle alone at POD 90. Histology is in progress.

TABLE 7

Nerve Conduction Studies and Muscle Force Data at Post-Operative Day 90

| | Sham | Trans | Trans + RN |
|---|---|---|---|
| Number of rats | 6 | 6 | 6 |
| Muscle Mass, (mg) | 148 ± 14.1 | 111 ± 14.6* | 133 ± 25.8 |
| CMAP Amplitude, (mV) | 8.7 ± 3.6 | 1.52 ± 1.0* | 3.9 ± 3.2* |
| Stimulus Threshold, (V) | 0.42 ± 0.05 | 1.5 ± 0.4* | 0.78 ± 0.5†,* |
| Area under CMAP, (mV * msec) | 13.6 ± 5.3 | 2.1 ± 1.1* | 8.6 ± 6.1* |
| Tetanic Force, (mN) | 586 ± 166 | 358 ± 295 | 789 ± 296† |

TABLE 7-continued

Nerve Conduction Studies and Muscle Force Data at Post-Operative Day 90

|  | Sham | Trans | Trans + RN |
|---|---|---|---|
| Motor Units, (#) | 8.3 ± 2.6 | 3.3 ± 1.7 | 8.4 ± 6.8 |
| Specific Force, (mN/mm$^2$) | 83.5 ± 11.7 | 49.4 ± 39.7 | 85.8 ± 28.32 |

Means ± SD;
*indicates significantly different ($p < 0.05$) from sham,
†indicates significantly different ($p < 0.05$) from transfer.
CMAP is an abbreviation for compound muscle action potential.

Nerve implantation into transferred muscle is the basis for biotic-abiotic, peripheral nerve interface. With this interface, increased sensitivity to electrical stimulation and tetanic force capacity when compared with transferred muscle alone occurs. These data imply that nerve implantation promoted successful neurotization. Successful neurotization of the peripheral nerve interface has significant implications for the design of biocompatible, long-lasting neural interfaces.

Example 8

Optimization of Peripheral Nerve-Prosthetic Device Interface Conduction and Flexibility Using Electro-Chemical Polymerization of PEDOT onto Decellular Nerve The following example, optimizes the process by which poly-3,4, ethylenedioxythiophene (PEDOT) is polymerized into decellular nerve scaffolding for interfacing to peripheral nerves. Our ultimate aim is to permanently implant peripheral nerve interfaces as ion, electron connectors between amputee stump nerve and prosthetic electronics. Optimizing PEDOT polymerization with DN increases conductivity while minimizing incompatible stiffness.

Decellular nerve (DN) is an FDA approved biomaterial (Axogen™) with flexible properties needed for successful permanent coaptation to peripheral nerve. As illustrated in FIG. 19, DN is polymerized with biocompatible electro-conductive PEDOT (which has been shown to add ionic and electrical conduction to biological materials. New electrochemical polymerization methods were used to vary PEDOT concentrations and to decrease dehydration. DN interfaces were then tested for impedance and charge density (n=5 per 6 groups). PN interfaces were also implanted as 20 mm peripheral nerve grafts. In-situ nerve conduction measurements immediately followed grafting.

PEDOT coated DN interface data show significant improvements in impedance and charge density for dehydrated concentrations as low as 10% and hydrated PEDOT concentrations as low as 1% when compared with DN alone ($\alpha=0.05$). These measurements were equivalent to 100% PEDOT concentrations on DN. Referring to Table 8 below, in-situ, nerve conduction measurements demonstrate that DN alone is a poor ion-electro-conductor while the addition of PEDOT allows DN interface scaffolds to compare favorably with the "gold standard" autograft nerve. Surgical handling characteristics for highly conductive hydrated PEDOT DN interface materials were rated 3 (pliable) while the dehydrated models were rated 1 (very stiff) when compared with autograft ratings of 4 (normal). FIG. 21 illustrates that polymerization with 25% dry PEDOT and 1% wet PEDOT adds significantly great charge density capacities to these Decellular nerve coated PEDOT grows when compared with the other materials listed in the respective plots (Fresh, 0% Dry, 2% Dry, and 10% Dry for comparison with the 25% Dry PEDOT group) and (Fresh nerve, 0% wet PEDOT on Decellular nerve, 0.02% Wet PEDOT on decellular nerve when compared with, and 10% Wet PEDOT on decellular nerve). The number of neuromuscular junctions formed per muscle was much greater for the neurotized muscle when compared with the non-neurotized transferred muscles, as illustrated in FIG. 22.

TABLE 8

Summary for In-Situ, Nerve Conduction Electro-diagnostic Properties Acutely Measured Across Coaptations of Decellular Nerve Interface Scaffolding (20 mm) in a Rat Peroneal Nerve Grafting Model.

|  | Main Effect | | | | |
|---|---|---|---|---|---|
| Variables | Intact Control (n = 33) | Autograft (n = 9) | DN (n = 3) | DPEDOT (n = 4) | HPEDOT (n = 5) |
| Latency (ms) | 1.3 ± 0.2 A | 1.6 ± 0.4 A | 40.9 ± 53.9 b | 1.2 ± 0.1 a | 1.8 ± 1.0 a |
| Amplitude (mV) | 17.6 ± 6.7 a, | 9.4 ± 11.8 a, b | 5.7 ± 9.8 A, 2 @ "0" | 14.4 ± 7.3 B, c | 11.4 ± 9.4 a,b |
| Velocity (M/s) | 25. ± 4.2 | 22 ± 5.0 | 12 ± 18 b | 36 ± 12 a | 29 ± 18 |
| Area 1-3 (mV * ms) | 18 ± 7 a | 7 ± 4 | 5 ± 12 b | 13 ± 5 | 8 ± 7 b |
| Rheobase (mA) | 0.22 ± 0.47 a | 1.72 ± 2.47 A | 55.5 ± 25.9 b | 4.5 ± 4.18 a | 2.52 ± 2.37 a (n = 6) |

TABLE 8-continued

Summary for In-Situ, Nerve Conduction Electro-diagnostic
Properties Acutely Measured Across Coaptations of Decellular Nerve
Interface Scaffolding (20 mm) in a Rat Peroneal Nerve Grafting Model.

| | Main Effect | | | | |
|---|---|---|---|---|---|
| Variables | Intact Control (n = 33) | Autograft (n = 9) | DN (n = 3) | DPEDOT (n = 4) | HPEDOT (n = 5) |
| Stimulation (mA) | 1.15 ± 3.86 a | 3.36 ± 5.09 C | 21.20 ± 11.78 b, d | 11.42 ± 9.61 b | 7.52 ± 4.52 (n = 6) |

Main Effect indicates type of interface coapted to the divided peroneal nerve. All grafts were 20 mm in length. 10-0 nylon suture was used for proximal and distal stump approximations to interface grafts.
Intact Control = no peroneal nerve lesions or graft;
Autograft = peroneal nerve section removed transposed 180° and grafted;
DN = Decellular Nerve alone as interface;
DPEDOT = dehydrated, PEDOT coated, DN, interface graft;
HPEDOT = hydrated, PEDOT coated, DN, interface graft. Stimulation was applied distal to the graft and at the sciatic notch at least 5 mm proximal to the proximal interface coaptation site. Repeated measures analysis of variance with distal measurement as the covariate.
Significance: $\alpha \leq 0.05$.
Letter pairs a-b or c-d indicate a significant difference exists between the pair. Bonferonni adjustments were made for multiple comparison post-hoc tests. Autograft, DPEDOT, and HPEDOT groups do not vary from one another for all electro-conductive variables. This lack of a difference is supported by statistical power, $\beta > 0.80$.
Abbreviations are:
milliseconds (ms),
millivolts (mV),
meters/second (M/s), and
milliamps (mA).

Based on the data above, low concentrations of PEDOT on DN interfaces can provide significant increases in ionic and electro-active properties which are comparable to 100% PEDOT coatings. DN interface pliability is closely maintained by continued hydration during PEDOT electrochemical polymerization without compromising any electro-conductivity.

Example 9

Nerve Regenerative Peripheral Nerve Interface: Recovery of Function

In the following example, a regenerative peripheral nerve interface (RPNI) for closed loop neural control of prostheses is developed. This interface integrates amputee's residual peripheral nerves with transferred skeletal muscle. The purposes are with respect to controls: a) to compare the electrical properties of RPNI at 1 and 3 months after implantation and b) to compare the resultant RPNI neurotization and muscle function at 3 months.

Rats (n=29) were divided into three groups: sham operated (Sham), free muscle transfer with no nerve innervation (MT), and muscle transfer with residual nerve implantation (RPNI). During sham surgeries, the right leg was dissected to expose the soleus muscle and then surgically closed. For both MT and RPNI groups the right soleus muscle was transferred between interstitial tissues of the left thigh, parallel with the femur. In the RPNI group the left peroneal nerve was divided and the proximal end sutured within the transferred muscle. After either 1 or 3 months of implantation the transferred muscles were tested using both nerve conduction studies (NCS) and muscle force testing. Histology was performed on nerves and muscles.

All surgical group muscles were viable at 1 and 3 months post-surgery; all data were analyzed. Referring to Tables 9 and 10 below, the RPNI at 3 months showed greatly improved functions over the 1 month RPNI values. Compound muscle action potential (CMAP) amplitude improved by 200%, CMAP area improved by 370%, and stimulus threshold voltage was beneficially decreased by 80%. RPNI values at 1 month showed distinctly less function when compared with Sham muscles but better function than the MT not neurotized controls. But by 3 months of recovery, RPNI improved function was no longer different from Sham muscles for CMAP amplitude, CMAP area, stimulus threshold, or maximal muscle force. RPNI neuromuscular junction density was 317% increase over Sham muscles. The negative control MT muscles showed significantly worse function than the Sham muscles at 3 month recovery for nerve conduction measurements. FIG. 22 depicts the successful reinnervation of transferred skeletal muscle neurotized by the residual stump of a peripheral nerve. Neuromuscular junctions (NMJ) indicate successful reinnervation of the muscle.

TABLE 9

Electromechanical function 3 months post-surgery

| | Sham (n = 7) | Muscle Transfer (n = 6) | RPNI (n = 6) |
|---|---|---|---|
| CMAP Amplitude, (mV) | 8.4 ± 2.8† | 1.7 ± 1.0* | 4.2 ± 3.4 |
| Stimulus Threshold, (V) | 0.41 ± 0.05 | 1.28 ± 0.71* | 1.10 ± 0.66 |
| Area CMAP, (mV*msec) | 21.8 ± 8.7 | 3.1 ± 2.7* | 12.8 ± 13.7 |
| Tetanic Force, (mN) | 586 ± 166 | 358 ± 295 | 789 ± 296† |
| Muscle mass, mg | 153 ± 18 | 111 ± 15* | 143 ± 34 |
| Motor Units, (#) | 8.3 ± 2.6 | 3.3 ± 1.7 | 8.4 ± 6.8 |
| Neuromuscular Junction Density (NMJ/mm$^2$) | 4.13 × 10$^4$ | 7.11 × 10$^4$ | 17.44 × 10$^4$* |

Data are means ± SD. $P \leq 0.05$.
*indicates different from Sham.
†indicates different from Muscle transfer alone.

TABLE 10

Nerve Conduction at 1 month post-surgery

|  | Sham (n = 4) | Muscle Transfer (n = 3) | RPNI (n = 3) |
|---|---|---|---|
| CMAP Amplitude, (mV) | 12.05 ± 7.8 | none | 1.4 ± 0.9 |
| Stimulus Threshold, (V) | 11.2 ± 12.4 | none | 6.0 ± 3.6 |
| Area CMAP, (mV * msec) | 29.9 ± 19.7 | none | 2.7 ± 2.2* |
| Muscle mass, mg | 159 ± 16 | 70.5 ± 25* | 139 ± 58 |

Data are means ± SD. $P \leq 0.05$.
*indicates different from Sham.

Functional neurotization follows nerve implantation into transferred muscle is the basis for RPNI use as a neural interface. Measured recovery of conduction and contractile functions within RPNI which compared favorably with Sham operated rats. These data confirm that neurotization occurs within the RPNI, allowing recovery of muscle responsivity to moderate stimulation and muscle contractile forces similar to sham muscle. These finding support RPNI use as an interface to neuroelectric prostheses.

Example 10

Long Term Effect of an Electroconductive Polymer on Injured Peripheral Nerve

In the following example, a regenerative peripheral nerve interface (RPNI) for closed-loop motor and sensory control of an artificial limb is developed. The RPNI uses the conductive polymer poly(3,4-ethylenedioxythiophene) (PEDOT) to facilitate nerve action potential propagation through the interface. This study validates a rat neuroma model and tests for the influence of PEDOT on nerve fiber anomalies. Rat peroneal nerves were divided and the proximal stumps were coapted to an acellular small intestinal submucosa (SIS). Two formulations of PEDOT were polymerized on the SIS: Dry PEDOT, a firm compound, and Wet PEDOT, a softer compound. Operated nerve groups were: Sham, Primary Repair, Divided Nerve, SIS, Dry PEDOT+SIS, and Wet PEDOT+SIS. Tactile sensitivity was evaluated using von Frey monofilaments. Nerve histomorphometry was evaluated. The Divided. Nerve group was more sensitive and had smaller nerve fibers than the Sham group, implying neuroma formation. Dry PEDOT+SIS group showed increased sensitivity at 3 months compared to SIS and smaller nerve fibers at 6 months. In contrast, the Wet PEDOT+SIS group showed less sensitivity compared to SIS and histomorphometry of these two groups was similar. Tactile analyses identified differences between rats with and without neuromas while histomorphometric analyses determined biocompatibility responses to PEDOT.

To ameliorate apparent poor biocompatibility of electrodes with biologic tissue, an interface design which incorporates the polymer poly(3,4-ethylenedioxythiophene), or PEDOT is studied. PEDOT is a highly conductive organic compound that can carry neural action potentials across nerve gap lengths as long as 20 mm at velocities, which exceed native nerve function. Its structural similarity to melanin, a pigment naturally present in the human body, also suggests biocompatibility, which has been borne out in multiple in vitro experiments. PEDOT is thus incorporated into the RPNI. This study tests the in situ biocompatibility of PEDOT within the interface design.

2. Materials and Methods

Though neuromas represent a significant obstacle to interfacing mechanical constructs with peripheral nerves, preventing neuroma formation is not the focus of this example. Instead, the effect of PEDOT on divided nerve endings is determined by quantifying the extent of nerve fiber anomalies as indications of biocompatibility. The von Frey monofilament scale indicates pain sensitivity, an indicator of neuroma formation, in the rat model.

PEDOT-Coated Scaffold

Scaffolds of 10 mm×2 mm, 8-ply acellularized small intestinal submucosa (SIS, Cook Surgical, Bloomington, Ind., USA) were polymerized with PEDOT. A chemical polymerization technique produced a brittle (Dry PEDOT) coating while an electrochemical polymerization technique produced a soft, gel (Wet PEDOT) coating.

2.1. Experimental Design and Procedure

This study used 48 eight-month-old retired breeder F344 strain male rats (Charles River Laboratories, Wilmington, Mass.). All procedures are approved by the Institutional Animal Care and Use Committee of the University of Michigan and were in accordance with the National Research Council's Guide for the Care and Use of Laboratory Animals.

Eight rats were randomly assigned to each one of six surgical groups: 1) Sham, 2) Primary Repair, 3) Divided Nerve, 4) SIS, 5) Dry PEDOT+SIS, and 6) Wet PEDOT+SIS (FIG. 1). In all groups, the left peroneal nerve was mobilized from the sciatic notch to the lateral compartment of the lower leg. In the Sham group, the wound was then closed without further manipulation. In the Primary Repair group, the nerve was transected 15 mm proximal to its entry into the lateral compartment of the lower leg, then immediately repaired with 10-0 nylon stitches.

In the remaining four groups, the nerve was transected at the same point, but the distal 15 mm of nerve were excised. The proximal stump was either left unrepaired (Divided Nerve) or coapted to a scaffolding of SIS, Dry PEDOT-coated SIS (Dry PEDOT+SIS), or Wet PEDOT-coated SIS (Wet PEDOT+SIS). The Divided Nerve group was included to confirm neuroma formation. The SIS group served as a control for the Dry PEDOT+SIS and Wet PEDOT+SIS groups. In all groups, the nerve was wrapped in a single-ply sheet of acellularized small intestinal submucosa (Cook Surgical, Bloomington, Ind., USA) (FIG. 2).

2.2. von Frey Evaluations von Frey monofilament testing for pain sensitivity was performed by a single observer at 3 and 6 months postoperatively. Lower von Frey thresholds reflect higher sensitivity to stimuli, implying pain due to nerve injury and neuroma formation within the RPNI. The von Frey monofilaments (Leica Microsystems, St. Louis, Mo.) were applied to the operative site in an up-down stepwise fashion to determine the amount of force required to elicit a withdrawal response from the animal. Stimulation was avoided while the animal was grooming, voiding, or otherwise distracted. von Frey data were calculated using Equation 1:

$$50\% \text{ g threshold} = \frac{10^{f+ks}}{10000} \quad \text{Equation}$$

f=value (in log units) of the final von Frey hair used, k=tabular value derived from the pattern of positive/negative responses, and s=mean difference (in log units) between stimuli.

To establish reproducibility of the metric, 13 rats were selected for a test-retest protocol. Ten were in the preoperative phase and 3 were in the postoperative phase. These von Frey measurements were conducted on two consecutive days.

2.3. Histologic Evaluation

After 6 months, rats were sacrificed for histologic evaluation. This time point allows for the formation of chronic neuromas in rats. Nerve tissue was removed from the coaptation site, fixed, embedded, and stained with toluidine blue. Samples from 24 animals (4 per group) were included in the histomorphometric analysis. Two representative high-power fields were quantified for each nerve by a blinded observer using MetaMorph Microscopy Automation and Image Analysis Software (Molecular Devices, Sunnyvale, Calif.). Measurements for nerve fiber axoplasm area, myelin area, total area, fiber diameter (short and long axis), and fiber count were collected. Derived variables, including G ratio (nerve fiber axoplasm area)/(nerve fiber area), fiber density (axon count)/(total nerve area), and percent neural area (sum of total fiber area)/(total nerve area) were also computed.

2.4. Tensiometry Evaluations

For bench tests of material stiffness, PEDOT was polymerized on single layer SIS using a previously described chemical polymerization technique. Samples of single layer SIS measuring 20 mm×5 mm×0.5 mm were tested. A total of 72 samples were prepared (24 for each of three groups: SIS alone (SIS), Dry PEDOT+SIS, and Wet PEDOT+SIS). Extensile tests (Instron Series 5500, Norwood Mass.) were performed by stretching 10 mm of each sample at a rate of 10 mm/minute until fracture occurred. Young's modulus, a measure of material compliance, as well as material stress and strain values from each sample were calculated and compared.

2.5. Data Analysis

SPSS Statistics (Version 17.0, SPSS Inc. Chicago, Ill.) was used for data analysis. The mean and standard deviations were determined for all dependent variables. A Kruskal-Wallis analysis was applied to the von Frey data. Post-hoc multiple comparison calculations were completed when the model was significant. Histological data were evaluated with a nested, one factor General Linear Model (GLM) in which the values for histological variables were nested by rat, with each rat belonging to one of the surgical groups (one factor). Tensiometry data were evaluated with a one factor GLM. When a GLM model was significant, multiple comparisons were conducted with Bonferroni corrections. Statistical significance was set at a<0.05 for two-way analyses. To assess the reproducibility of the von Frey methodology, Pearson correlation coefficients were calculated. To visually compare metrics with different units side by side, standardized Z-scores were computed for von Frey testing, fiber short diameter, and percent neural area.

3. Results

3.1. Demographics

As illustrated in Table 11, no differences were noted between any experimental groups for preoperative or postoperative weights. All rats gained weight during the postoperative period. No animals died during the operative procedure or experienced postoperative wound infections. At the terminal operation, adhesions were noted in all groups, including the Sham.

TABLE 11

Preoperative and Postoperative Rat Demographics

| Sham (n = 8) | Primary Repair (n = 8) | Divided Nerve (n = 8) | SIS (n = 8) | Dry PEDOT + SIS (n = 8) | Wet PEDOT + SIS (n = 8) |
|---|---|---|---|---|---|
| 187 ± 2 | 184 ± 2 | 187 ± 3 | 190 ± 4 | 190 ± 3 | 185 ± 2 |
| 366 ± 51 | 388 ± 55 | 395 ± 28 | 372 ± 48 | 387 ± 28 | 399.8 ± 35 |
| 444 ± 45 | 441 ± 58 | 432 ± 31 | 434 ± 22 | 427 ± 37 | 453 ± 37 |

No significant demographic differences were found.
Data are means ± SD.
Abbreviations are:
SIS, Porcine small intestinal submucosa;
PEDOT•poly(3,4-ethylenedioxythiophene);
POD, postoperative day. a < 0.05.

Several animals were not available for evaluation at the 6 month time point. Two animals from the Divided Nerve group died prior to evaluation at 6 months. Data for one animal from the SIS group and two from the Primary Repair group were not included due to technical concerns.

3.2. von Frey Testing

The von Frey measurement is expressed as 50% gram threshold. Lower von Frey thresholds reflect higher sensitivity, which implies painful neuroma formation within the RPNI. As illustrated in Table 12, at 3 and 6 months of recovery, the Divided Nerve group was significantly more sensitive than the Sham group, indicating neuromas formed when the nerve was divided but not repaired.

TABLE 12

Tactile Sensitivity by von Frey Monofilament Testing at 3 and 6 months Postoperatively.

| | VON FREY SENSITIVITY (GRAMS) BY SURGICAL GROUP | | | | | |
|---|---|---|---|---|---|---|
| | Sham | Primary Repair | Divided Nerve | SIS | Dry PEDOT + SIS | Wet PEDOT + SIS |
| @ 3 mo | 0.63 ± 0.76 (n = 8) | 0.62 ± 0.96 (n = 8) | 0.1 ± 0.15* (n = 8) | 0.22 ± 0.33 (n = 8) | 0.01 ± 0.02*†[1]‡ (n = 8) | 0.32 ± 0.32[2] (n = 8) |
| @ 6 mo | 1.03 ± 1.08 (n = 8) | 0.15 ± 0.19* (n = 6) | 0.07 ± 0.1* (n = 6) | 0.23 ± 0.32 (n = 7) | 0.13 ± 0.13* (n = 7) | 0.15 ± 0.15* (n = 8) |

Data reflects 50% gram threshold with von Frey up-down evaluations.
Data are means ± SD.
Abbreviations are:
SIS, Porcine small intestinal submucosa;
PEDOT, poly(3,4-ethylenedioxythiophene).
*different than sham.
†different than Primary Repair.
‡different than Divided Nerve.
[1]different than SIS, $\alpha < 0.07$.
[2]different than Dry PEDOT + SIS.
$\alpha < 0.05$ unless otherwise specified.

At 3 months, the Dry PEDOT+SIS group was the most sensitive among the Sham, Primary Repair, Divided Nerve, and SIS groups. In contrast, at 3 months the Wet PEDOT+SIS group was less sensitive than the Dry PEDOT+SIS and did not differ from the SIS group (power=0.61, a=0.1). At 6 months of recovery, all groups except the SIS group expressed more sensitivity than the Sham group. The Wet PEDOT+SIS and Dry PEDOT+SIS groups did not show differences in sensitivity when compared with the SIS group at 6 months. Thus, sensitivity initially increased at 3 months in the presence of Dry PEDOT, but by 6 months of recovery there were no discernible differences in pain sensitivity between the Divided Nerve, Wet PEDOT+SIS, and Dry PEDOT+SIS groups.

Results for von Frey test-retest reliability yielded a correlation coefficient of r=0.77 between scores for day 1 and day 2 tests for each animal. This correlation indicates strong test repeatability.

3.3. Histologic Findings

FIG. 25 illustrates the qualitative differences in nerve fiber diameter, fiber density, myelin thickness, and fascicular organization, apparent between experimental groups. The presence of PEDOT did not appear to have a significant impact on the amount of inflammation, fibrosis, or disorganization of the nerve fibers in the RPNIs. There were few macrophages, lymphocytes, or neutrophils in any given RPNI.

FIG. 26A-26F depicts histology of Rat Peroneal Nerve Samples. Sham shows large nerve fibers with thick myelin sheaths (FIG. 26A), Primary Repair has smaller fibers and less myelin (FIG. 26B), Divided Nerve (FIG. 26C), SIS (FIG. 26D), Dry PEDOT+SIS (FIG. 26E), Wet PEDOT+SIS (FIG. 26F). Toluidine-blue stained samples imaged at 1000×.

Table 13 below shows the quantitative histological data, including nerve total area, nerve fiber myelin area, nerve fiber axoplasm area, nerve fiber long diameter, and nerve fiber short diameter.

TABLE 13

Quantitative Nerve Fiber Histomorphometry at 6 Months Postoperatively.

| | SURGICAL GROUPS | | | | | |
|---|---|---|---|---|---|---|
| | Sham (n = 3669) | Primary Repair (n = 4207) | Divided Nerve (n = 4207) | SIS (n = 3153) | Dry PEDOT + SIS (n = 4179) | Wet PEDOI + SIS (n = 2184) |
| Nerve Fiber Total Area ($\mu m^2$) | 46.04 ± 36.4 | 15.2 ± 17.9* | 9.6 ± 8.3*† | 14.1 ± 18.5*‡ | 8.6 ± 8.1*†[1] | 12.3 ± 16.7*†‡[2] |
| Nerve Fiber Myelin Area ($\mu m^2$) | 20.1 ± 12.2 | 5.7 ± 4.5* | 4.3 ± 2.9*† | 6.3 ± 6.7*†‡ | 3.9 ± 2.5*†[1] | 5.4 ± 4.3*‡[2] |
| Nerve Fiber Axoplasm Area ($\mu m^2$) | 25.9 ± 25.8 | 9.5 ± 13.8* | 5.3 ± 5.8*† | 7.9 ± 12.3*†‡ | 4.7 ± 5.9*†[1] | 6.9 ± 13*†‡[2] |
| Nerve Fiber Long Diameter ($\mu m$) | 10.8 ± 4.2 | 5.3 ± 2.8* | 4.8 ± 2.00*† | 5.5 ± 2.9*‡ | 4.3 ± 2.02*†‡[1] | 5.5 ± 3.6*‡[2] |

TABLE 13-continued

Quantitative Nerve Fiber Histomorphometry at 6 Months Postoperatively.

| | SURGICAL GROUPS | | | | | |
|---|---|---|---|---|---|---|
| | Sham (n = 3669) | Primary Repair (n = 4207) | Divided Nerve (n = 4207) | SIS (n = 3153) | Dry PEDOT + SIS (n = 4179) | Wet PEDOI + SIS (n = 2184) |
| Nerve Fiber Short Diameter (μm) | 6.2 ± 2.5 | 3.6 ± 1.7* | 2.8 ± 1.1*† | 3.3 ± 1.6*†‡ | 2.8 ± 1.1*†[1] | 3.1 ± 1.4*†‡[2] |

Data are means ± SD.
See Methods for calculations.
Abbreviations are:
SIS, Porcine small intestinal submucosa;
PEDOT, poly(3,4-ethylenedioxythiophene).
*different than Sham.
†different than Primary Repair.
‡different than Divided Nerve.
[1]different than SIS.
[2]different than Dry PEDOT + SIS.
$\alpha < 0.05$.

The Sham group had the largest values for all variables measured while the Divided Nerve and Dry PEDOT+SIS groups had the smallest values. Small regenerating nerve fibers indicate irritation at the sprouting nerve endings and could be indicative of neuroma formation. In contrast, the Wet PEDOT+SIS group showed significantly larger nerve fiber averages than the Divided Nerve and Dry PEDOT+SIS groups. Therefore, signs of nerve regeneration in the Wet PEDOT+SIS group indicate less irritation than in the Dry PEDOT+SIS group.

Several derived histomorphometric variables—G ratio, fiber density, and percent neural area were also calculated in Table 14 below.

G ratio is inversely related to the proportion of nerve fiber myelin area: thus, more myelin yields a lower G Ratio. All experimental groups with an unrepaired divided nerve had smaller G ratios, and therefore greater myelin area, than the Sham. These ratio figures may indicate ongoing nerve regeneration in the experimental groups. No statistical differences were found for fiber density among the groups. Lastly, the Sham group was found to have the highest percent neural area, predictably indicating optimal nerve recovery following surgical intervention compared to the experimental groups.

TABLE 14

Derived Quantitative Histomorphometry at 6 Months Postoperatively.

| | SURGICAL GROUPS | | | | | |
|---|---|---|---|---|---|---|
| | Sham | Primary Repair | Divided Nerve | SIS | Dry PEDOT + SIS | Wet PEDOT + SIS |
| G-Ratio | 0.51 ± 0.12 (n = 1985) | 0.52 ± 0.16 (n = 3669) | 0.5 ± 0.12*† (n = 4207) | 0.49 ± 0.12*†‡ (n = 3153) | 0.47 ± 0.12*†‡[1] (n = 4179) | 0.47 ± 0.12*†‡[1] (n = 2184) |
| Fiber Density (fibers/μm$^2$) (n = 4 each group) | 0.012 ± 0.0023 | 0.020 ± 0.010 | 0.021 ± 0.018 | .017 ± 0.0036 | 0.025 ± 0.0099 | 0.012 ± 0.0027 |
| Fiber Density (fibers/um^2) n = 4 each group | 0.012 ± 0.0023 | 0.020 ± 0.010 | 0.021 ± 0.018 | 0.017 ± 0.0036 | 0.025 ± 0.0099 | 0.012 ± 0.0027 |
| % Neural Area n = 4 each group | 46.0 ± 10.6 | 26.6 ± 14.7 | 18.3 ± 10.3* | 21.9 ± 7.3* | 19.7 ± 5.4* | 13.2 ± 4.5* |

Data are means ± SD.
See Methods for calculations.
Abbreviations are:
SIS, Porcine small intesitinal submucosa;
PEDOT, poly(3,4-ethylenedioxythiophene).
*indicates different than Sham.
†different than Primary Repair.
‡different than Divided Nerve.
[1]different than SIS.
[2]different than Dry PEDOT + SIS.
$\alpha < 0.05$.

3.4. Tensiometry

All 72 samples prepared for tensiometry were tested. Several samples—one from the SIS group, one from the Dry PEDOT+SIS group, and two from the Wet PEDOT+SIS group were excluded for technical reasons. The data are summarized in Table 15.

TABLE 15

Tensiometry of SIS and SIS polymerized with Dry PEDOT or Wet PEDOT

| | SURGICAL GROUPS | | |
|---|---|---|---|
| | SIS | Dry PEDOT + SIS | Wet PEDOT + SIS |
| Sample Size | 23 | 23 | 22 |
| Young's Modulus (Mpa) | 6.89 ± 2.76 | 10.17 ± 5.78* | 4.36 ± 2.65† |
| Size (mm by mm) | 10 by 5 | 10 by 5 | 10 by 5.9 ± 0.3 |
| Stress (MPa) | 3.99 ± 1.26 | 3.65 ± 1.67 | 2.60 ± 1.42* |
| Strain | 90.22 ± 27.32 | 55.41 ± 17.45* | 87.51 ± 29.29† |
| Mass (mg) | 23.97 ± 6.06 | 22.01 ± 8.20 | 34.30 ± 8.16 |

A smaller Young's modulus value indicates more compliance in a material.
Data are means ± SD.
Abbreviations are:
SIS, small intestinal submucosa;
PEDOT·poly(3,4-ethylenedioxythiophene).
*Indicates different from SIS alone.
†Different from Dry PEDOT + SIS. a < 0.05.

The Wet PEDOT+SIS group proved more elastic than the Dry PEDOT+SIS material and similar to the SIS alone (p $\leq$ 0.05). Wet PEDOT+SIS could not endure as much stress as the SIS on its own, but was more extensible. Lower compliance and higher strain tolerance are desirable characteristics for materials that contact flexible peripheral nerves, as has been previously demonstrated.

4. Discussion

Neuroma formation is quantified using von Frey testing and select histomorphometry. The Sham group contained normal nerve and exhibited high von Frey thresholds and large nerve fibers, while the Divided Nerve group exhibited the most robust neuroma formation, characterized by low von Frey thresholds and small nerve fibers.

FIG. 23 depicts experimental groups with the Rat Peroneal Nerve. Sham: nerve exposed but left intact. Primary Repair: nerve divided, then immediately repaired. Divided Nerve: nerve divided, and distal segment excised. SIS: nerve divided and coapted to a scaffolding of SIS; distal segment excised. Dry PEDOT+SIS: nerve divided and coapted to a scaffolding of SIS coated with Dry PEDOT; distal segment excised. Wet PEDOT+SIS: nerve divided and coapted to a scaffolding of SIS coated with Wet PEDOT; distal segment excised.

FIG. 24 depicts a schematic of the peripheral nerve interface. The peroneal nerve is divided, then coapted to a scaffold that has been polymerized with a conductive polymer.

The wet PEDOT+SIS construct appears to have minimal influence on lesioned nerve fiber morphology and pain sensation (i.e., neuroma formation). The addition of Wet PEDOT did not affect pain sensitivity as measured by von Frey testing at either 3 or 6 months when compared with the SIS group, see Table 11 above. This finding is echoed in histologic data for nerve fiber long diameter and percent neural area. In addition, histomorphometric measurements revealed significantly smaller values for total nerve fiber area, nerve fiber myelin area, nerve fiber axoplasm area, and nerve fiber short diameter (p $\leq$ 0.05) for the Divided Nerve group when compared with the Wet PEDOT+SIS group, confirming nerve fiber anomalies were minimal. The similarity between the behavioral and histomorphometric data is illustrated in FIG. 25. Wet PEDOT+SIS even seemed to have a mitigating effect on neuroma formation compared to the Divided Nerve group—in every nerve fiber measurement, Wet PEDOT+SIS had fewer indications of neuroma formation than the Divided Nerve group as illustrated in Table 13.

In contrast, the Dry PEDOT+SIS construct performed similarly to the Divided Nerve group and consistently worse than the control SIS group. Nerve fiber quantitative histomorphometry revealed that Dry PEDOT+SIS had either smaller or statistically indistinguishable nerve fiber sizes compared to the Divided Nerve group. Similarly, von Frey testing at 3 months yielded comparable values for the Dry PEDOT+SIS and Divided Nerve groups, indicating that both were more sensitive than every other group tested.

In an effort to understand the observed difference in the performance of Dry PEDOT+SIS and Wet PEDOT+SIS in vivo, extensile properties were compared. Tensiometry testing findings indicated that Wet PEDOT was significantly more elastic than Dry PEDOT. Combined with the von Frey and histomorphometric findings, these data confirm that elastic materials (Wet PEDOT+SIS) are more compatible with biologic tissues than inelastic materials (Dry PEDOT+SIS).

The model used in this example is robust and reproducible. There were no demographic differences between the six experimental groups. Although behavioral data can be notoriously variable, the von Frey data was reproducible in a comparison of two consecutive days of testing. The Sham group, showcasing normal nerve, and the Divided Nerve group, designed to foster neuroma formation, showed significant differences for every behavioral and histomorphometric metric.

There were several limitations to this study. First, the study was designed to evaluate the chronic phase of neuroma and nerve fiber morphology, so there is limited data on the acute phase biologic response of the animals. In the model, the divided nerve was left in situ without additional markers or surgical modifications, which could create ambiguity about the neuroma site. In addition, the sensitivity of the skin incision could confound the animal's neuroma response. However, the approach was surgically similar to an amputation. The statistical differences between the positive (Divided Nerve) and negative (Sham) control groups appear robust despite these limitations.

Some groups note that while von Frey monofilaments are rated based on force, in practice they exert pressures disproportionate to their force differences because of independent variability in cross-sectional area. To address this concern, an up-down technique for the von Frey monofilaments was used.

In various aspects, the present disclosure provides prosthetic interfaces capable of integration with closed-loop neural control. Conductive polymers provide enhancing nerve interfaces, and this example indicates their favorable biocompatibility profile. The findings also indicate that polymerization techniques and mechanical differences may alter the body's tolerance of these foreign components.

Example 11

Nerve Regeneration in the Presence of Conductive Polymers

Interfacing the human nervous system with prosthetic limb electronics requires signal translation from a biologic to an abiotic environment and vice versa. Information exchange occurs in the form of ionic (nerve) and electronic (machine) current. The conductive polymer, 3,4 polyethylenedioxythiophene (PEDOT) carries both electronic and ionic transmission. PEDOT has recently been used for biomedical applications, including neural cell signaling and neural interfaces. It is demonstrated that peripheral nerves successfully regenerate across a critical-length gap in the presence of PEDOT. It is evaluated regenerated nerve conductivity, end-organ function and histology when in the presence of PEDOT. These are the first reported data of regenerating peripheral nerve fibers under the long-term influence of PEDOT.

An amputee's residual peripheral nerves with processors that receive and transmit signals for prostheses control is interfaced. As discussed above, PEDOT (3,4-polyethylenedioxythiophene) is an anisotropic, conductive polymer that beneficially reduces tissue impedance. PEDOT can be polymerized into nonconductive, processed decellular nerve (DN) leaving it highly conductive but stiff (DryPEDOT), or, less conductive but pliable (WetPEDOT). It was tested in nerve regeneration in a rat peripheral nerve interface (PNI) environment. PEDOT biocompatibility is evaluated by histology of nerve fiber morphology after regeneration through reconstructed nerve conduits including PEDOT.

Fisher 344 rats were utilized for the study. Animal care and operative procedures were performed in accordance with the *United States Public Health Service Guide for the Care of Laboratory Animals* (NIH Publication Number 85-23, 1985). A 15 mm, peroneal nerve gap was reconstructed with one of five nerve derived materials: Sham, Autograft, DN, DryPEDOT, and WetPEDOT, or Gap (not reconstructed); (n=8/group). A single layer of acellular submucosa surrounded each graft forming a conduit as in our peripheral nerve interfaces. After 90 days, evaluations were completed for muscle force, nerve conduction, and quantitative midgraft morphology. A modified nerve morphology grading tool was also utilized for qualitative investigation purposes.

Results for gap reconstruction groups only, as no nerves bridged the gap in the Gap group. As illustrated in FIG. 27, nerve fibers are successfully regenerated in each group as confirmed by evoked compound muscle action potential presence. Conduction velocity was fastest for DryPEDOT and slowest for WetPEDOT groups. Muscle force was also recovered in each group as illustrated in Table 16.

TABLE 16

Statistical Summary of Muscle Force and Motor Action.

| | Surgical Groups | | | | | |
|---|---|---|---|---|---|---|
| | Sham | Autograft | Decellular Nerve | Dry PEDOT | Wet PEDOT | Gap |
| Number of Subjects | n = 8 | n = 8 | n = 8 | n = 8 | n = 8 | n = 8 |
| Maximum isometric tetanic force (mN) | 3119.3 ± 571 | 1592 ± 520* | 783 ± 686* | 232 ± 2111*† | 82 ± 60.2*† | 0 |
| Action potential velocity (m/s) | 13.4 ± 2.7 | 13.9 ± 3.8 | 9.3 ± 1.5*† | 19.6 ± 2.6*†‡ | 5.8 ± 0.9*†§ | 0 |

Values listed are mean ± SD, $p < 0.05$,
*indicates difference vs. Sham,
†indicates difference vs. Autograft,
‡indicates different from Decellular nerve,
§indicates difference from dry PEDOT Nerve morphology rankings from normal to still reorganizing were: Sham>Autograft>DN>WetPEDOT>DryPEDOT, illustrated in Table 17.

TABLE 17

Statistical Summary of Qualitative and Quantitative Nerve Histology by Reconstruction Type.

| | Surgical Groups | | | | | |
|---|---|---|---|---|---|---|
| | Sham (n = 8) | Autograft (n = 8) | Decellular Nerve (n = 8) | Dry PEDOT (n = 8) | Wet PEDOT (n = 8) | Gap (n = 8) |
| Nerve histology grade | 6 ± 0 | 9.2 ± 1.9* | 12.8 ± 2.6*† | 20.5 ± 1.4*†‡ | 16.2 ± 3.2*†‡§ | 22.0 ± 0*†‡ |
| Axon Count | 877 ± 461 | 863 ± 297 | 552 ± 256 | 169 ± 240† | 190 ± 100† | 0 |

TABLE 17-continued

Statistical Summary of Qualitative and Quantitative Nerve Histology by Reconstruction Type.

| | Surgical Groups | | | | | |
|---|---|---|---|---|---|---|
| | Sham (n = 8) | Autograft (n = 8) | Decellular Nerve (n = 8) | Dry PEDOT (n = 8) | Wet PEDOT (n = 8) | Gap (n = 8) |
| Neural Area ($\mu m^2$) | 15169 ± 5639 | 9408.9 ± 5191 | 4442 ± 2810 | 998.2 ± 1380† | 12888 ± 815 | 0 |
| Axon Density ($1/\mu m^2$) | 0.019 ± 0.005 | 0.022 ± 0.012 | 0.011 ± 0.008 | 0.003 ± 0.004*† | 0.004 ± 0.002 | 0 |
| Percent of Neural Area (%) | 34.8 ± 9.97 | 21.3 ± 7.55 | 9.04 ± 6.33 | 1.68 ± 2.41*† | 2.73 ± 1.84*† | 0 |

For qualitative analysis nerve specimens were evaluated with modified versions of the grading tool that was originally described before Murji 2008. With this grading tool low score indicates better nerve morphology. Quantitative analysis was performed using a digital image analyzer (Metamorph Offline, Molecular Devices, Sunny vale, CA.
Values listed are mean ± SD, $\alpha < 0.05$, 2-tailed
*indicates difference from Sham,
†indicates difference from Autograft,
‡indicates difference from Decellular Nerve,
§indicates different from Dry PEDOT.

Electron micrographs of DryPEDOT show dry PEDOT greatly reduces DN conduit diameter. A significant increase in nerve conduction velocity occurs with the polymerization of dry PEDOT on decellular nerve. While not limiting the present teachings to any particular theory, this type of improvement in conduction velocity can be attributed to the well described characteristics of PEDOT which increase charge density and decrease conduction impedance. Muscle force testing shows that dry and wet PEDOT are equally capable of allowing reinnervation of muscle end-organs and recovery of contractile functional. To evaluate nerve histology, a modified grading tool was used in which higher ratings indicate poorer nerve morphology. The ratings for DryPEDOT and WetPEDOT conduit cross sections indicated more regeneration impairment than the DN conduits. PEDOT deposition may cause mechanical obstruction acellular nerve channels leading to limitations on nerve regeneration. Quantitative nerve histology showed that both DryPEDOT and WetPEDOT conduits had similar means for axon count, nerve fiber density, neural area, and percent neural area. Axon counts for the DryPEDOT and WetPEDOT were smaller than those for the autograft. Thus both the dry and wet polymerized PEDOT conduits had the same impact on nerve regeneration. However, addition of wet or dry PEDOT to decellular nerve did negatively affect the quality of total nerve regeneration when rated against regeneration through DN conduits.

Based on these results above a deposition of PEDOT by either dry or wet polymerization techniques is compatible with peripheral nerve fiber regeneration. The evoked action potential velocity through nerves regenerated in an environment of dry PEDOT show faster velocity at 3 months of regeneration than sham and the other experimental groups. When coupled with previously demonstrated ionic-to-electronic signal translation with using PEDOT, this study paves the way for highly conductive and biocompatible peripheral nerve interfaces, which can ultimately lead to high-fidelity, patient-controlled prosthetics with multiple degrees of freedom.

Example 12

Conduction Properties of Decellularized Nerve Biomaterials

The purpose of this example is to optimize poly(3,4,-ethylenedioxythiophene) (PEDOT) polymerization into decellular nerve scaffolding for interfacing to peripheral nerves. It is desirable to have permanently implanted highly conductive peripheral nerve interfaces between amputee, stump, nerve fascicles and prosthetic electronics. Decellular nerve (DN) scaffolds are an FDA approved biomaterial (Axogen™) with the flexible tensile properties needed for successful permanent coaptation to peripheral nerves. Biocompatible, electroconductive, PEDOT facilitates electrical conduction through PEDOT coated acellular muscle. New electrochemical methods are used to polymerize various PEDOT concentrations into DN scaffolds without the need for a final dehydration step. DN scaffolds were then tested for electrical impedance and charge density. PEDOT coated DN scaffold materials were also implanted as 15-20 mm peripheral nerve grafts. Measurement of in-situ nerve conduction immediately followed grafting. DN showed significant improvements in impedance for dehydrated and hydrated, DN, polymerized with moderate and low PEDOT concentrations when they were compared with DN alone ($a \leq 0.05$). These measurements were equivalent to those for DN with maximal PEDOT concentrations. In-situ, nerve conduction measurements demonstrated that DN alone is a poor electro-conductor while the addition of PEDOT allows DN scaffold grafts to compare favorably with the "gold standard" autograft illustrated in Table 18 below. Surgical handling characteristics for conductive hydrated PEDOT DN scaffolds were rated 3 (pliable) while the dehydrated models were rated 1 (very stiff) when compared with autograft ratings of 4 (normal). Low concentrations of PEDOT on DN scaffolds provided significant increases in electro active properties which were comparable to the densest PEDOT coatings. DN pliability was closely maintained by continued hydration during PEDOT electrochemical polymerization without compromising electroconductivity.

II. Materials and Methods

A. Overview of Experimental Design

The purpose was to optimize the electrical fidelity and gain seen when PEDOT is polymerized on DN scaffolding while minimizing the sharp rigidity which accompanies highly conductive but compact concentrations of PEDOT.

Bench Test and In-Situ Experimental Designs:

PEDOT can be deposited onto DN scaffolds by methods that either include dehydration steps (chemical method) or allow scaffolds to remain continuously hydrated (electrochemical method). Using each method, various concentrations of PEDOT are polymerized onto DN scaffolds. DN scaffolds with bench tests which measured impedance (fidelity) and cyclic voltammetry to determine charge transfer capacity (gain in amplitude) were tested. Then, based on the bench tests, the "best" concentrations for dehydrated and hydrated DN scaffolds are selected and in-situ tests are conducted for measuring nerve conduction properties (biological signal conductivity).

Rat sciatic nerves were harvested at the University of Michigan and decellularized by Axogen™. The DN scaffolds were polymerized with PEDOT. A chemical polymerization method used an EDOT monomer (Clevios™ M, H.C. Starck, Coldwater, Mich.) and iron chloride as a dopant. The DN scaffolds are dehydrated for adherence of the PEDOT. EDOT solutions were made in low (Low), moderate (Mod), and high (High) concentrations which corresponded to the amount of PEDOT deposited. The electrochemical method for PEDOT deposition used a PEDOT polymer and polystyrenesulfonic acid (Clevios™ P, H.C. Starck, Coldwater, Mich.); DN scaffold dehydration was not needed. Low and Mod concentrations of PEDOT were deposited using the method which allowed constant hydration of the DN scaffolds B. Measurement of Test Material Impedance and Specific Charge Density Electrical impedance spectroscopy (EIS) testing was applied to determine electrode impedance (Frequency Response Analyzer; Version 4.9.007; Eco Chemie B.V.; Utrecht, The Netherlands) and cyclic voltammetry (CV) to determine charge transfer capacity (n~4 per 9 groups) (General Purpose Electrochemical System, Version 4.9.007, Eco Chemie B.V., Utrecht, The Netherlands). Graphs were viewed using MatLab (Version 7.8.0.347 R2009a; MatchWorks, Inc). Materials tested were between 15 and 20 mm in length. Impedance values were sampled for frequencies of 10, 100, and 1000 Hz. For CV, a scan rate of 10 mV/s was used and the potential on the working electrode was swept between −1.0 to 1.0 V. Specific charge density was calculated by dividing the charge transfer capacity by each sample's surface area (surface area of a cylinder).

C. Measurement of Nerve Conduction

For in-situ measurements, dehydrated (DPEDOT) and hydrated (HPEDOT) DN scaffolds were polymerized with moderate concentrations of PEDOT. Selection of the moderate concentration for further testing is based on favorable results from the bench tests. Five experimental groups were tested; these groups were: Intact nerve, Autograft, DN (hydrated as shipped frozen), DPEDOT, and HPEDOT. Using 10-0 nylon suture, DN scaffold materials were sewn to the ends of divided, rat, peroneal nerve as 15-20 mm peripheral nerve grafts (n≥5 per 5 groups). Measurement of in-situ nerve conduction immediately followed grafting (Synergy T2X System, Viasys NeuroCare, Madison, Wis.). Stimulation was applied with a bipolar electrode placed on the nerve proximal to the nerve graft and as close to the sciatic notch as possible. Muscle electromyographic (EMG) responses were recorded with a needle electrode in the ex-tensor digitorum longus muscle located distal to the nerve graft. Reference and ground needle electrodes were placed distal to the recording electrode. Values recorded were EMG response latency, maximal amplitude, and spike area; as well as nerve conduction velocity, rheobase, and the stimulation amperage equal to 20% greater than that used to maximize EMG.

D. Graft Stiffness Rating Scale

Graft stiffness was rated using a scale from 4 to 0. A score of 4 meant the DN scaffold handled as native nerve; 3=pliable, slight resistance to bending; 2= rigid, resistant to needle insertion; 1=brittle, very stiff, cut the suture; and 0 meant a needle could not be placed through the material.

E. Animal Care and Compliance

Rats used were male Fischer-344 rats which were retired as breeders (Charles River Laboratory, Kingston, N.Y.). All procedures were approved by the Institutional Animal Care and Use Committee of the University of Michigan and were in strict accordance with the National Research Council's Guide for the Care and Use of Laboratory Animals. For all surgical procedures, rats were given an analgesic (buprenorphine, 0.05 mg/kg) prior to anesthesia with sodium pentobarbital (65 mg/kg). All rats were euthanized with an UCUCA approved procedure.

F. Statistical Analysis

A one-way analysis of variance (ANOVA) was performed, followed by Tukey's post hoc test to determine significant differences between experimental groups in the bench test and in the in-situ studies. A p value with a≤0.05 was considered to be significant.

Data in FIG. 29 indicate that deposition of PEDOT on DN scaffolds significantly lowers (improves) impedance across all the hydrated as well as all dehydrated DN materials when compared to dehydrated DN with the exception of the Low dehydrated DN scaffold. Specific charge density was increased (improved) only for the Mo dehydrated DN when compared with dehydrated DN as illustrated in FIG. 30. Some PEDOT broke off the dehydrated DN scaffolds during EIS and CV testing. No charge density could be measured for three of seven scaffolds in the High dehydrated DN group. These zero scores, most likely due to PEDOT cracking and falling off, were included in the statistics and ex-plain the drop in specific charge density seen for this group when compared with the Mod dehydrated DN group. The EIS and CV data taken together may indicate there was a ceiling effect on how much PEDOT was enough.

In-situ, nerve conduction measurements demonstrated that hydrated DN scaffolds appear to be poor electroconductors. While intact nerve was best, addition of PEDOT allowed grafted DN scaffolds to compare favorably with the "graft gold standard," autograft nerve as illustrated in Table 18.

TABLE 18

Summary for In-Situ, Nerve Conduction Electrodiagnostic Properties Acutely Measured Across Coaptations of Decellular Nerve Interface Scaffolding (15-20 mm) in a Rat Peroneal Nerve Grafting Model.

| | Main Effect | | | | |
|---|---|---|---|---|---|
| Variables | Intact Control (n = 33) | Autograft (n = 9) | DN (n = 3) | DPEDOT (n = 4) | HPEDOT (n = 5) |
| Latency (ms) | 1.3 ± 0.2 a | 1.6 ± 0.4 a | 40.9 ± 53.9 b | 1.2 ± 0.1 a | 1.8 ± 1.0 a |
| Amplitude (mV) | 17.6 ± 6.7 a, | 9.4 ± 11.8 a, b | 5.7 ± 9.8 A, 2 @ "0" | 14.4 ± 7.3 B,c | 11.4 ± 9.4 a,b |
| Velocity (M/s) | 25. ± 4.2 | 22 ± 5.0 | 12 ± 18b | 36 ± 12a | 29 ± 18 |
| Area 1-3 (mV * ms) | 18 ± 7a | 7 ± 4a | 5 ± 12 b | 13 ± 5 | 8 ± 7 b |
| Rheobase (mA) | 0.22 ± 0.47 a | 1.72 ± 2.47 a | 55.5 ± 25.9 b | 4.5 ± 4.18 a | 2.52 ± 2.37 a (n = 6) |
| Stimulation (mA) | 1.15 ± 3.86 a | 3.36 ± 5.09 c | 21.20 ± 11.78 b, d | 11.42 ± 9.61 b | 7.52 ± 4.52 (n = 6) |

Main Effect indicates type of interface coapted to the divided peroneal nerve. All grafts were 20 mm in length. 10-0 nylon suture was used for proximal and distal stump approximations to interface grafts.
Intact Control = no peroneal nerve lesions or graft;
Autograft = peroneal nerve section removed transposed 180° and grafted;
DN = Decellular Nerve alone as interface;
DPEDOT = dehydrated, PEDOT coated, DN, interface graft;
HPEDOT = hydrated, PEDOT coated, DN, interface graft. Stimulation was applied distal to the graft and at the sciatic notch at least 5 mm proximal to the proximal interface coaptation site. Repeated measures analysis of variance with distal measurement as the covariate.
Significance: $\alpha \leq 0.05$.
Letter pairs a-b or c-d indicate a significant difference exists between the pair. Bonferroni adjustments were made for multiple comparison post-hoc tests. Autograft, DPEDOT, and HPEDOT groups do not vary from one another for all electro-conductive variables. This lack of a difference is supported by statistical power, $\beta > 0.80$.
Abbreviations are:
milliseconds (ms),
millivolts (mV),
meters/second (M/s), and
milliamps (mA).

Autograft, DPEDOT, and HPEDOT grafts did not vary from each other for all EMG data (latency, maximal amplitude, spike area) and nerve conduction measurements (velocity, rheobase, and the stimulation voltage). Statistical power for these findings exceeded $\beta$=0.80. Though not significant, greater stimulation amperage is needed to initiate a twitch response (rheobase) and maximal response amplitude for conduction to pass through the DN scaffold graft with PEDOT when compared with the Autograft.

Surgical handling characteristics for the hydrated DN scaffold and the Autograft nerve were rated 4 (as native nerve). The highly conductive HPEDOT DN scaffolds were rated 3 (pliable). DPEDOT DN scaffolds were rated 2 (rigid). The dehydrated DN with High PEDOT group from the bench studies was rated 1 (very stiff). Polymerization of PEDOT by the electrochemical method allows DN scaffolds to remain hydrated and therefore to behave almost like native nerve during surgery.

Bench test findings for impedance indicate that PEDOT does confer improvements in conduction fidelity and signal to noise ratio. In-situ tests show that PEDOT deposition on DN facilitated biological signal conduction across a nerve gap. However, the bench cyclic voltammetry results did not show convincing improvements in charge transfer capacity (signal gain) for the PEDOT coated DN scaffolds. The electrochemical polymerization process did allow the DN scaffolds to remain pliable following polymerization with PEDOT.

Bench tests measured improvements in impedance for DN scaffolds polymerized with PEDOT. Lower impedance indicated the electrical signal has better fidelity or signal to noise ratio. Devices with low impedance generally have lower overall power requirements leading to extended battery life. Decreased impedance is a favorable quality for a PNI scaffold.

Specific charge density measurements did not increase significantly for all PEDOT coated DN scaffolds except for the moderately high coated dehydrated PEDOT DN group. Charge density is thought to determine charge transfer capacity or gain. A PNI needs to contribute some as yet unknown quantity of charge transfer. PEDOT is known to accumulate greater charge density because the fluffy PEDOT structure increases surface area as illustrated in FIG. 28. However, too much specific charge density could damage the native peripheral nerve. However, the meaning and benefits of charge density is not fully understood at this juncture. DN scaffolding alone, although not a good electrical conductor, may be a fine base material for a PNI. Peripheral nerves grow through it and, though it is an allograft material, inflammation and immune response to it are minimal.

This is the first study to show that addition of PEDOT to DN allowed action potential type signals to pass across a 15 to 20 mm nerve graft. A 15 mm distance is the desired length for a PNI. Higher stimulation was needed to initiate a twitch response and a maximal response across the graft because signals are obstructed by scarring at two nerves to graft coaptation sites. Whether the "biologic like" signals across the graft are purely electrical, ionic, or a mixture of the two is undefined.

The bench studies and the in-situ nerve conduction studies in some of the Examples above indicate that moderate concentrations of PEDOT on DN are enough to reduce impedance and facilitate conduction through the DN scaffold. Reduced PEDOT concentrations along with the electrochemical deposition allowed the DN scaffold to remain pliable. Still slightly higher concentration of PEDOT in the hydrated samples should be possible. Implanting this DN scaffold as part of a PNI is a realistic goal. Pliability allows DNs to move with the peripheral.

Low concentrations of PEDOT on DN scaffolds can provide significant increases in electroactive properties which are comparable to maximal High PEDOT coatings. DN pliability is closely maintained by continued hydration during PEDOT electrochemical polymerization without com-promising electro conductivity.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The disclosure of all patents and patent applications cited in this disclosure are incorporated by reference herein.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. A regenerative peripheral nerve interface (RPNI) for a subject comprising:
    an insulating substrate and at least one metallic electrode disposed on or in the insulating substrate, so that the insulating substrate and the at least one metallic electrode define a thin-film array;
    a layer of decellularized biotic material comprising decellularized small intestinal submucosa (SIS); and
    at least one conductive polymer.

2. The regenerative peripheral nerve interface of claim 1, wherein the at least one conductive polymer is electrically polymerized through the layer of decellularized biotic material to form a soft, mechanically compliant interface with the thin-film array.

3. The regenerative peripheral nerve interface of claim 1, wherein the layer of decellularized biotic material is a coating disposed on a portion of a surface of the at least one metallic electrode.

4. The regenerative peripheral nerve interface of claim 1, wherein the at least one conductive polymer is disposed on a portion of a surface of the at least one metallic electrode.

5. The regenerative peripheral nerve interface of claim 1, wherein the insulating substrate is selected from a group consisting of: poly-paraxylylene (parylene), polyimide, silicon dioxide, and combinations thereof.

6. The regenerative peripheral nerve interface of claim 1, wherein the at least one metallic electrode comprises a metallic material or a non-metallic material, wherein the metallic material is selected from a group consisting of Gold (Au), Platinum (Pt), Iridium (Ir), Palladium (Pd), Tungsten (W), Stainless Steel (SS), Indium-Tin-Oxide (ITO), Zinc, Titanium (Ti), alloys, oxides, and combinations thereof, and the non-metallic material is selected from a group consisting of: poly(3,4-ethylenedioxythiophene) (PEDOT), poly(pyrrole), polyaniline, polyacetylene, polythiophene, ester derivative 3,4-propylenedioxythiophene (ProDOT), natural or synthetic melanin, derivatives, and combinations thereof.

7. The regenerative peripheral nerve interface of claim 1, wherein the thin-film array comprises 1 to 32 electrodes and has a diameter of less than or equal to about 1.5 mm, a length of less than or equal to about 3.6 mm, a width of less than or equal to about 3.6 mm, and a thickness of less than or equal to 15 μm.

8. The regenerative peripheral nerve interface of claim 1, wherein the thin-film array has a length of less than or equal to about 1.5 mm.

9. The regenerative peripheral nerve interface of claim 1, wherein the at least one conductive polymer comprises a first conductive polymer and a second conductive polymer.

10. The regenerative peripheral nerve interface of claim 9, wherein the first conductive polymer and the second conductive polymer are independently selected from a group consisting of: poly(3,4-ethylenedioxythiophene) (PEDOT), poly(pyrrole), polyaniline, polyacetylene, polythiophene, ester derivative 3,4-propylenedioxythiophene (ProDOT), natural or synthetic melanin, derivatives, and combinations thereof.

11. The regenerative peripheral nerve interface of claim 9, wherein the first conductive polymer or the second conductive polymer comprises poly(3,4-ethylenedioxythiophene) (PEDOT).

12. The regenerative peripheral nerve interface of claim 1, further comprising a layer of muscle tissue contacting the regenerative peripheral nerve interface.

13. The regenerative peripheral nerve interface of claim 12, wherein the regenerative peripheral nerve interface is implanted on at least one nerve stump of a peripheral nerve of the subject.

14. The regenerative peripheral nerve interface of claim 12, wherein the regenerative peripheral nerve interface is connected to at least one sensor configured to control a prosthetic device.

15. A method of forming a regenerative peripheral nerve interface, the method comprising:
forming at least one metallic electrode in or on an insulating substrate, wherein the at least one metallic electrode and the insulating substrate define a thin-film array;
depositing a first layer of a conductive polymer onto a first portion of a surface of the at least one metallic electrode; and
coating a second portion of the surface of the at least one metallic electrode with a layer of decellularized biotic material comprising decellularized small intestinal submucosa (SIS) to form the regenerative peripheral nerve interface.

16. The method of claim 15, further comprising electrically polymerizing a second conductive polymer through the layer of decellularized biotic material.

17. The method of claim 15, further comprising implanting the regenerative peripheral nerve interface on at least one nerve ending of a peripheral nerve of a subject.

18. The method of claim 17, wherein the implanted regenerative peripheral nerve interface is biologically stable for about a year to the lifetime of the subject.

19. The method of claim 15, wherein the regenerative peripheral nerve interface is capable of connecting with at least one sensor of a prosthetic device.

20. The method of claim 15, wherein the regenerative peripheral nerve interface is connected to at least one sensor of a prosthetic device in a subject, and the regenerative peripheral nerve interface is capable of controlling the prosthetic device.

21. A regenerative peripheral nerve interface device for interfacing between a peripheral nerve of a subject and a prosthetic device, the regenerative peripheral nerve interface device comprising:
an insulating substrate;
at least one metallic electrode disposed in or on the insulating substrate defining a thin-film array, a portion of a surface of the at least one metallic electrode having a layer of a first conductive polymer;
a layer of decellularized small intestinal submucosa (SIS) coating a portion of the surface of the at least one metallic electrode, wherein a second conductive polymer is electrochemically polymerized through the SIS to form a regenerative peripheral nerve interface; and
a layer of muscle tissue contacting the regenerative peripheral nerve interface.

22. The regenerative peripheral nerve interface device of claim 21, wherein the regenerative peripheral nerve interface device is implanted on at least one nerve stump of the peripheral nerve of the subject.

23. The regenerative peripheral nerve interface device of claim 21, wherein the regenerative peripheral nerve interface device is connected to at least one sensor configured to control the prosthetic device.

* * * * *